(12) United States Patent
Basiji et al.

(10) Patent No.: US 6,249,341 B1
(45) Date of Patent: Jun. 19, 2001

(54) IMAGING AND ANALYZING PARAMETERS OF SMALL MOVING OBJECTS SUCH AS CELLS

(75) Inventors: David A. Basiji, North Seattle; William E. Ortyn, Bainbridge Island, both of WA (US)

(73) Assignee: Amnis Corporation, Seattle, WA (US)

( * ) Notice: Subject to any disclaimer, the term of this patent is extended or adjusted under 35 U.S.C. 154(b) by 0 days.

(21) Appl. No.: 09/490,478

(22) Filed: Jan. 24, 2000

Related U.S. Application Data
(60) Provisional application No. 60/117,203, filed on Jan. 25, 1999.

(51) Int. Cl.[7] .............................. G01J 3/14; G01J 3/443; G01N 21/47; G01N 21/64
(52) U.S. Cl. ......................... 356/73; 356/326; 356/338; 356/328; 356/318
(58) Field of Search ............................ 356/73, 319, 326, 356/328, 338, 317, 318

(56) References Cited

U.S. PATENT DOCUMENTS

| | | | |
|---|---|---|---|
| Re. 35,868 | 8/1998 | Kosaka | 250/574 |
| 4,786,165 | 11/1988 | Yamamoto et al. | 356/23 |
| 5,141,609 * | 8/1992 | Sweedler et al. | 356/344 |
| 5,159,397 | 10/1992 | Kosaka et al. | 356/73 |
| 5,159,398 | 10/1992 | Maekawa et al. | 356/73 |
| 5,159,642 | 10/1992 | Kosaka | 382/6 |
| 5,247,339 | 9/1993 | Ogino | 356/73 |
| 5,272,354 | 12/1993 | Kosaka | 250/574 |
| 5,422,712 | 6/1995 | Ogino | 356/73 |
| 5,444,527 | 8/1995 | Kosaka | 356/73 |
| 5,471,294 | 11/1995 | Ogino | 356/73 |
| 5,548,395 | 8/1996 | Kosaka | 356/73 |
| 5,596,401 | 1/1997 | Kusuzawa | 356/23 |
| 5,633,503 | 5/1997 | Kosaka | 250/458.1 |
| 5,644,388 | 7/1997 | Maekawa et al. | 356/73 |
| 5,754,291 * | 5/1998 | Kain | 356/73 |
| 5,760,899 * | 6/1998 | Eismann | 356/326 |
| 5,831,723 | 11/1998 | Kubota et al. | 356/73 |

FOREIGN PATENT DOCUMENTS

WO 00/42412    7/2000   (WO) ........................... G01N 15/02

OTHER PUBLICATIONS

Ong, S.–H.; Horne, D.; Yeung, C.–K.; Nickolls, P.; Cole, T. "Development of an Image Flow Cytometer." Analytical and Quantitative Cytology and Histology. XIVth International Conference on Medical and Biological Engineering and the VIIth International Conference on Medical Physics, Espoo, Finland. Aug. 11–15, 1985. pp. 375–382.

Ong, Sim Heng. "Development of a System for Imaging and Classifying Biological Cells in a Flow Cytometer." Doctor of Philosophy Thesis. University of Sydney, School of Electrical Engineering. Aug. 1985.

* cited by examiner

Primary Examiner—F. L. Evans
(74) Attorney, Agent, or Firm—Ronald M. Anderson

(57) ABSTRACT

Light from an object such as a cell moving through an imaging system is collected and dispersed so that it can be imaged onto a time delay and integration (TDI) detector. The light can be emitted from a luminous object or can be light from a light source that has been scattered by the object or can be a fluorescent emission by one or more FISH probes, frequently used to detect substances within cells. Further, light that is absorbed or reflected by the object can also be used to produce images for determining specific characteristics of the object. The movement of the object matches the rate at which a signal is read from the TDI detector. Multiple objects passing through the imaging system can be imaged, producing both scatter images and spectrally dispersed images at different locations on one or more TDI detectors.

76 Claims, 11 Drawing Sheets

IMAGING AND ANALYZING PARAMETERS OF SMALL MOVING OBJECTS SUCH AS CELLS

RELATED APPLICATIONS

This application is based on prior copending provisional patent application Ser. No. 60/117,203, filed on Jan. 25, 1999, the benefit of the filing date of which is hereby claimed under 35 U.S.C. § 119(e).

FIELD OF THE INVENTION

This invention generally relates to imaging moving objects or particles for purposes of analysis and detection, and more specifically, to a system and method for determining and analyzing the morphology of moving objects, such as cells, and for detecting the presence and composition of Fluorescence In-Situ Hybridization (FISH) probes within cells.

BACKGROUND OF THE INVENTION

There are a number of biological and medical applications that are currently impractical due to limitations in cell and particle analysis technology. Examples of such biological applications include battle field monitoring of known airborne toxins, as well as the monitoring of cultured cells to detect the presence of both known and unknown toxins. Medical applications include non-invasive prenatal genetic testing and routine cancer screening via the detection and analysis of rare cells (i.e., low rate of occurrence) in peripheral blood. All of these applications require an analysis system with the following principal characteristics:

1. high speed measurement;
2. the ability to process very large or continuous samples;
3. high spectral resolution and bandwidth;
4. good spatial resolution;
5. high sensitivity; and
6. low measurement variation.

In prenatal testing, the target cells are fetal cells that cross the placental barrier into the mother's bloodstream. In cancer screening, the target cells are sloughed into the bloodstream from nascent cancerous tumors. In both of these applications of this technology, the target cells may be present in the blood at concentrations of one to five cells per billion. This concentration yields approximately 20–100 target cells in a typical 20 ml blood sample. The extreme rarity of the targeted cells demands that any detection and analysis system employed in these applications be capable of processing an enriched sample of approximately 100 million cells within a few hours, corresponding to a minimum throughput of 10,000 cells per second. Cell processing includes the determination of cellular morphology parameters such as overall size, nuclear size, nuclear shape and optical density, the detection and characterization of numerous fluorescent markers and FISH probes, the quantification of the total amount of DNA in the nucleus, and the detection of other cellular components such as fetal hemoglobin. To accomplish these processing tasks, the system must be able to collect cell images with a spatial resolution of approximately 1 micron. Likewise, the system must have high spectral resolution and bandwidth to differentiate four or more fluorescent colors. Since some probes may label important cellular features with only a few thousand fluorescent molecules, the system must have high sensitivity and good measurement consistency to differentiate very weak signals.

The predominant research laboratory protocols for non-invasive prenatal diagnosis employ a complex series of process steps that include gradient centrifugation to remove unnucleated cells, high-speed cell sorting for fetal cell enrichment, and fluorescence microscopy for fetal cell identification and genetic analysis. These protocols often yield little or no fetal cells for analysis, because a fraction of the fetal culls are lost at each step of the protocol. Nevertheless, the protocols cannot be simplified because of limitations in existing analysis technology. Ideally, fetal cell identification and analysis would be performed in a few hours by a high speed cell sorter having the necessary speed and sample handling capacity. This ideal is not possible with conventional systems, because conventional cell sorters lack the necessary imaging abilities, sensitivity, and repeatability to reliably identify fetal cells and enumerate the number and color of FISH probes used to make the diagnosis. Therefore, under current protocols, cells must be sorted onto slides and examined using fluorescence microscopy to establish their fetal origin and make a genetic diagnosis. The combination of low fetal cell yields and lengthy processing times precludes the clinical application of non-invasive fetal testing with existing technology.

No technology prior to the present invention incorporates all six of the principal characteristics of a viable fetal cell or cancer analysis system. In the prior art, there have been advances that might be applied to these applications, but significant limitations still remain.

A paper published by Ong et al. [Anal. Quant. Cytol. Histol., 9(5):375-82] describes the use of a time-delay and integration (TDI) detector in an imaging flow cytometer. A TDI detector is any pixellated device in which the signal produced in response to radiation directed at the device can be caused to move in a controlled fashion. Typically, the pixels of a TDI detector are arranged in rows and columns, and the signal is moved from row to row in synchrony with a moving image projected onto the device, allowing an extended integration time without blurring. The approach disclosed by Ong et al. advanced the art by addressing the need for spatial resolution and high sensitivity for cells in flow. However, this approach does not address the remaining principal characteristics. The authors of this paper cite an operating speed of 10 cells per second and a theoretical speed limitation of 500 cells per second, which is at least an order of magnitude slower than is required for non-invasive fetal testing. In addition, the system has no spectral resolution; laser scatter and fluorescence light are collected by the imaging system indiscriminately.

In more recent developments, U.S. Pat. No. 5,644,388 discloses an alternative approach to an imaging flow cytometer. The patent discloses the use of a frame-based image collection approach in which a video camera views cells in flow, in a freeze frame fashion. This method requires the image collection system to be synchronized with the presence of cells in the imaging area, unlike the case of TDI, wherein the detector readout rate is synchronized with the velocity of the cells. When a cell is imaged with the frame-based method, the integration period must be very short to prevent blurring. A short integration time is achieved either with a strobed light source, or a continuous light source combined with a shuttered detector. In either case, the short integration time reduces the signal-to-noise ratio and the ultimate sensitivity of the approach. Further, frame-based cameras require time to transfer data out of the camera, during which no images are acquired, and cells of interest can escape detection. Finally, like the work of Ong et al, this patent makes no provisions for acquiring data over a large spectral bandwidth and with sufficient spectral resolution to simultaneously resolve numerous and differently colored fluorescent probes and FISH spots.

Spectral discrimination is addressed in U.S. Pat. No. 5,422,712, in which the spectra of particles suspended in a fluid are collected as the particles flow through a detection region. However, there is no spatial representation of the object in the system disclosed in this patent, because the object is defocussed at the detector. In this system, light is collected from the object and an image is created at an intermediate aperture. The light continues through the aperture to a spectral dispersing element, which disperses the light spectrally along the axis of flow. The dispersed light is applied to an image intensifier in which it is amplified, and the light signal output from the image intensifier is finally directed to frame-based detector. At the intermediate aperture, prior to spectral dispersion, the image represents the spatial distribution of light in object space. The spatial distribution is blurred as the light propagates past the image plane, through the spectral dispersing element and onto the image intensifier. Because there is no provision for re-imaging the intermediate aperture at the intensifier, the resulting signal distribution at the intensifier represents only the spectral distribution of the light and does not preserve the spatial distribution of the light from the object. The loss of spatial information limits the utility of the invention for applications such as fetal cell analysis. If multiple identical FISH spots are present in a cell, their spectra can be ascertained using this approach, but the number of spots cannot be determined. In addition, this approach disperses the wavelength spectrum parallel to the axis of flow. If two particles are illuminated in the flow axis, their spectra can overlap on the detector. To prevent this problem, the patent discloses that a very short illumination height in the flow axis is used. The short illumination height decreases integration time, which necessitates the use of the image intensifier. Further, the short illumination height limits throughput by preventing the simultaneous imaging of multiple cells in the flow axis.

Accordingly, it will be apparent that an improved technique is desired that resolves the limitations of the conventional approaches discussed above. It is expected that the new approach developed to address these problems in the prior art will also have application to the analysis of other types of moving objects besides cells and may be implemented in different configurations to meet the specific requirements of disparate applications of the technology.

SUMMARY OF THE INVENTION

The present invention is directed to an imaging system that is adapted to determine one or more characteristics of an object from an image of the object. There is relative movement between the object and the imaging system, and although it is contemplated that either (or both) may be in motion, the object will preferably move while the imaging system will be fixed. In addition, it should also be understood that while much of the following summary and the corresponding claims recite "an object," it is clearly contemplated that the present invention is preferably intended to be used with a plurality of objects and is particularly useful in connection with imaging a stream of objects.

The present invention provides a method and apparatus for the analysis of rare cells in the blood for the purposes of non-invasive fetal cell diagnosis and cancer screening, as well as other applications. To achieve such functions, the present invention is capable of rapidly collecting data from a large cell population with high sensitivity and low measurement variation. These data include simultaneous spatial and spectral images covering a large bandwidth at high resolution. Further, the present invention preserves the spatial origin of the spectral information gathered from the object.

Several different embodiments of the imaging system are provided. One preferred form of the invention includes a collection lens disposed so that light traveling from the object is collimated by passing through the collection lens and travels along a collection path. A spectral dispersing element is disposed in the collection path so as to spectrally disperse the collimated light that has passed through the collection lens in a plane substantially orthogonal to a direction of relative movement between the object and the imaging system, producing spectrally dispersed light. (As noted above, the object or the imaging system or both can be in motion relative to the other and for the sake of simplicity, this relative movement is hereinafter referred to simply as "the movement.") An imaging lens is disposed to receive the spectrally dispersed light, producing an image from the spectrally dispersed light. Also included is a TDI detector disposed to receive the image produced by the imaging lens. As the movement occurs, the image of the object produced by the imaging lens moves from row to row across the TDI detector. The TDI detector produces an output signal that is indicative of at least one characteristic of the object, by integrating light from at least a portion of the object over time.

As a result of light collimation by the collection lens in this embodiment, all light emitted from a first point in the object travels in parallel rays. Light emitted from a second point in the object will also travel in parallel rays, but at a different angle relative to light from the first point. In this manner, spatial information in the object is transformed by the collection lens into angular information in the collection path. The spectral dispersing element acts on the collimated light such that different spectral components leave the spectral dispersing element at different angles, in a plane substantially orthogonal to the direction of the movement between the object and the imaging system. In this manner, both spatial and spectral information in the object are transformed into angular information. The imaging lens acts on the light from the dispersing element to transform different light angles into different positions on the detector. Spatial information is preserved by the system since light from the different positions in the object is projected to different positions on the detector, in both axes. In addition, light of different spectral composition that originates from the object is projected to different positions on the detector in an axis substantially orthogonal to the movement. In this manner, the spatial information from the object is preserved while simultaneously collecting spectral information covering a large bandwidth at high resolution.

FIG. 16 further illustrates the simultaneous collection of spectral and spatial information by the present invention, when imaging male and female cells 200 and 208, respectively. Light of shorter wavelength, such as green laser scatter 212, will be focussed on the left side of the TDI detector. Light of slightly longer wavelength, such as yellow fluorescence 214 from a cell nucleus 202 or 210, will be laterally offset to the right. Light of still longer wavelengths, such as orange fluorescence 216 from an X-chromosome FISH probe and red fluorescence 218 from a Y-chromosome FISH probe, will be focussed progressively farther to the right on the TDI detector. In this manner, different components of a cell that fluoresce at different wavelengths will be focussed at different locations on the TDI detector, while preserving the spatial information of those components. Each component image may be broadened laterally due to the width of its associated fluorescence emission spectrum. However, this broadening can be corrected based upon a priori knowledge of the emission spectra. Deconvolution of the emission spectrum from the broadened component image will yield an undistorted component image. Further, since the spectral dispersion characteristics of the spectral dispersing element are known, the lateral offsets of the different color component images can be corrected to reconstruct an accurate image of the cell. Using this embodiment of the invention, high spatial resolution information can be collected simultaneously with high spectral resolution over several hundred nanometers of spectral bandwidth. It should clear to those skilled in the art that invention can be employed to enumerate numerous and multicolored FISH probes to simultaneously determine many characteristics from cells.

The use of a TDI detector in the present invention results in an extended imaging region along the axis of motion and a correspondingly long integration time. Several light sources can be simultaneously projected into the imaging region, increasing the amount of light incident upon objects therein. In addition, the combination of an extended imaging region and the orthogonal orientation of the spectral dispersion axis relative to the axis of the motion allows multiple objects to be imaged simultaneously. The long integration time and parallel image acquisition of this embodiment allows sensitive and consistent imaging performance to be combined with high throughput.

There are several alternative ways to provide light from the object. In one case, the light from the object comprises an unstimulated emission from the object, i.e., the object emits light without requiring a light source to stimulate the emission. In another embodiment, a light source is disposed to provide an incident light that illuminates the object. In this case, the object may scatter the incident light so that the light scattered from the object at least in part passes through the collection lens, or the incident light illuminating the object may stimulate the object to emit the light that passes through the collection lens. Further, the incident light may at least be partially absorbed by the object, so that the light passing through the collection lens does not include a portion of the light absorbed by the object. Finally, the incident light from the light source may be reflected from the object toward the collection lens. The light source or sources that are used preferably comprise at least one of a coherent light source, a noncoherent light source, a pulsed light source, and a continuous light source.

Spectral dispersion may be accomplished by many means, including a prism or grating. Further, although one preferred form of the invention employs a spectral dispersing element, the present invention is not limited to imaging the spectral dispersion of light. Alternatively, a dispersing element can be used to disperse light as a function of position, angle, polarization, phase, and other characteristics.

The object may be entrained within a fluid stream that moves the object past the collection lens, or alternatively, can be carried on a support, or simply move without the benefit of a support or flowing medium. Moreover, the present invention is not limited to the imaging of microscopic or small objects.

The TDI detector preferably responds to the image of the object by producing a signal that propagates across the TDI detector. Pixels of a typical TDI detector are arranged in rows and columns, and the signal propagates from row to row. However, the present invention is not limited to TDI detectors employing a rectilinear arrangement of pixels (e.g., a microchannel plate-based TDI detector). A propagation rate of the signal across the TDI detector can either be synchronized with a motion of the image of the object on the TDI detector as a result of the movement, or can be non-synchronized with the movement.

Other aspects of the present invention are directed to methods for imaging an object. These methods implement steps that are generally consistent with the imaging system discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with th accompanying drawings, wherein.

Figure 6:
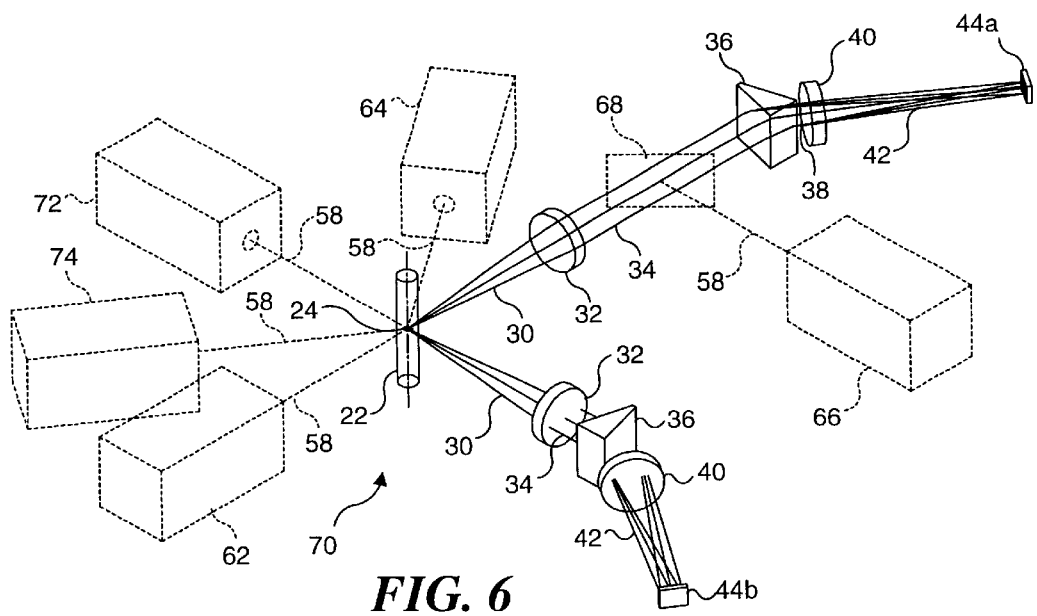
Figure 7:
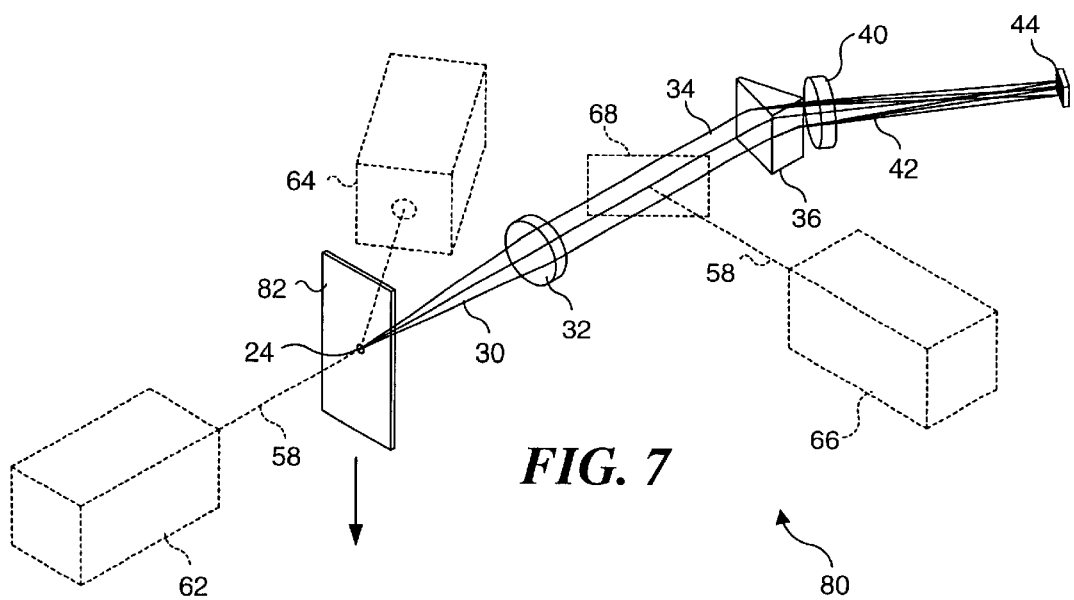
Figure 8A:
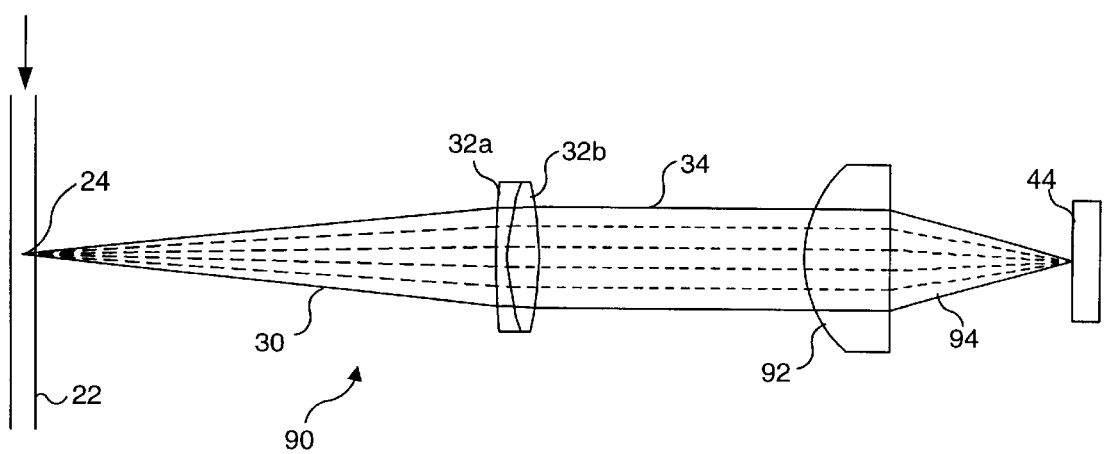
Figure 8B:
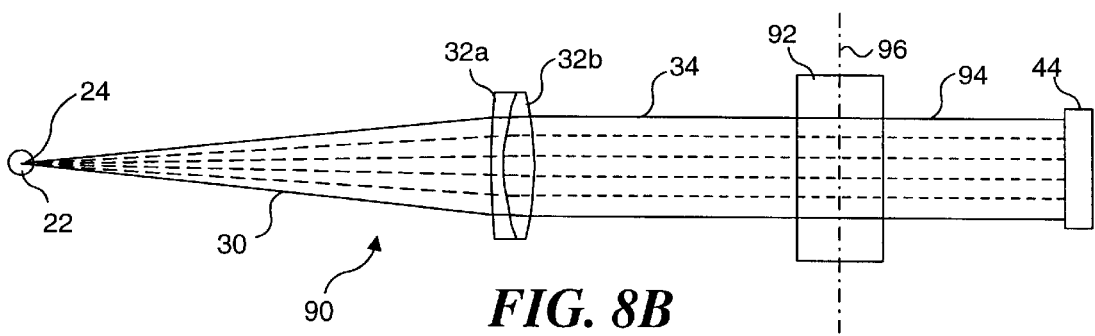
Figure 9:
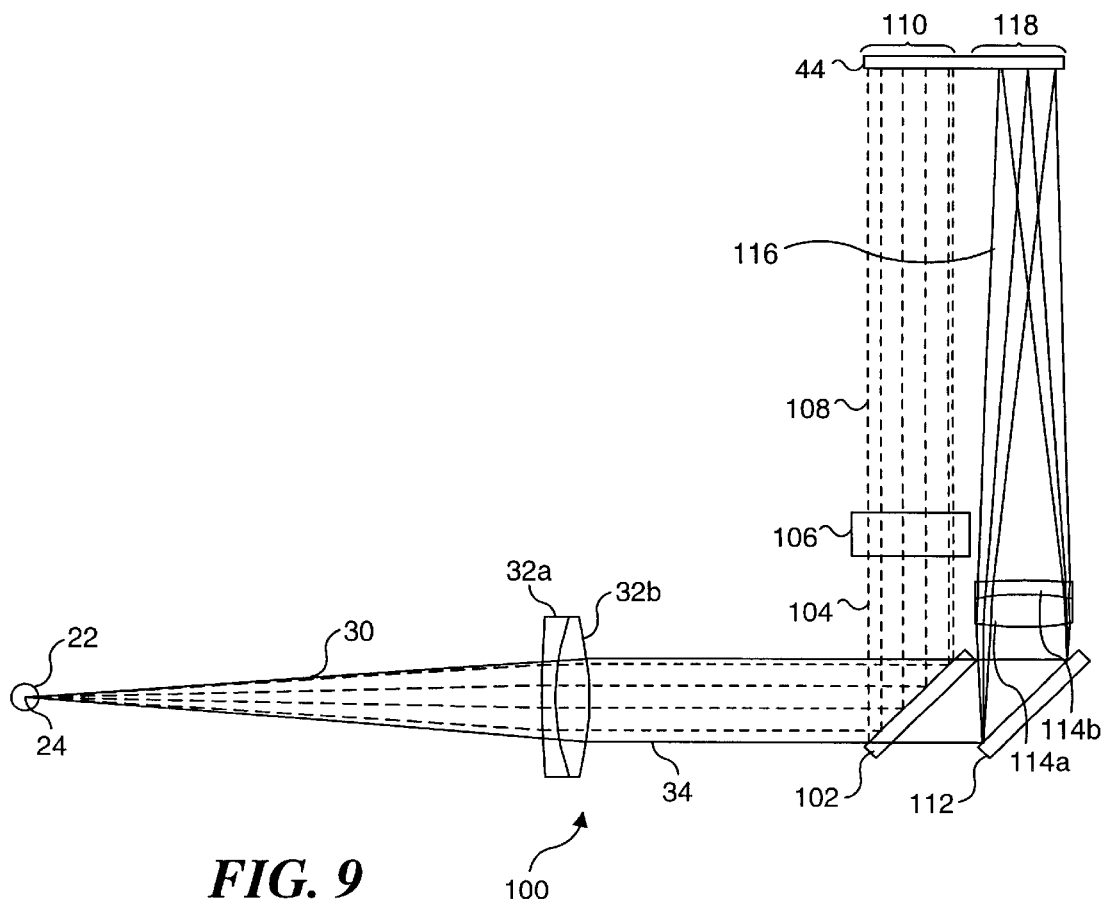
Figure 10:
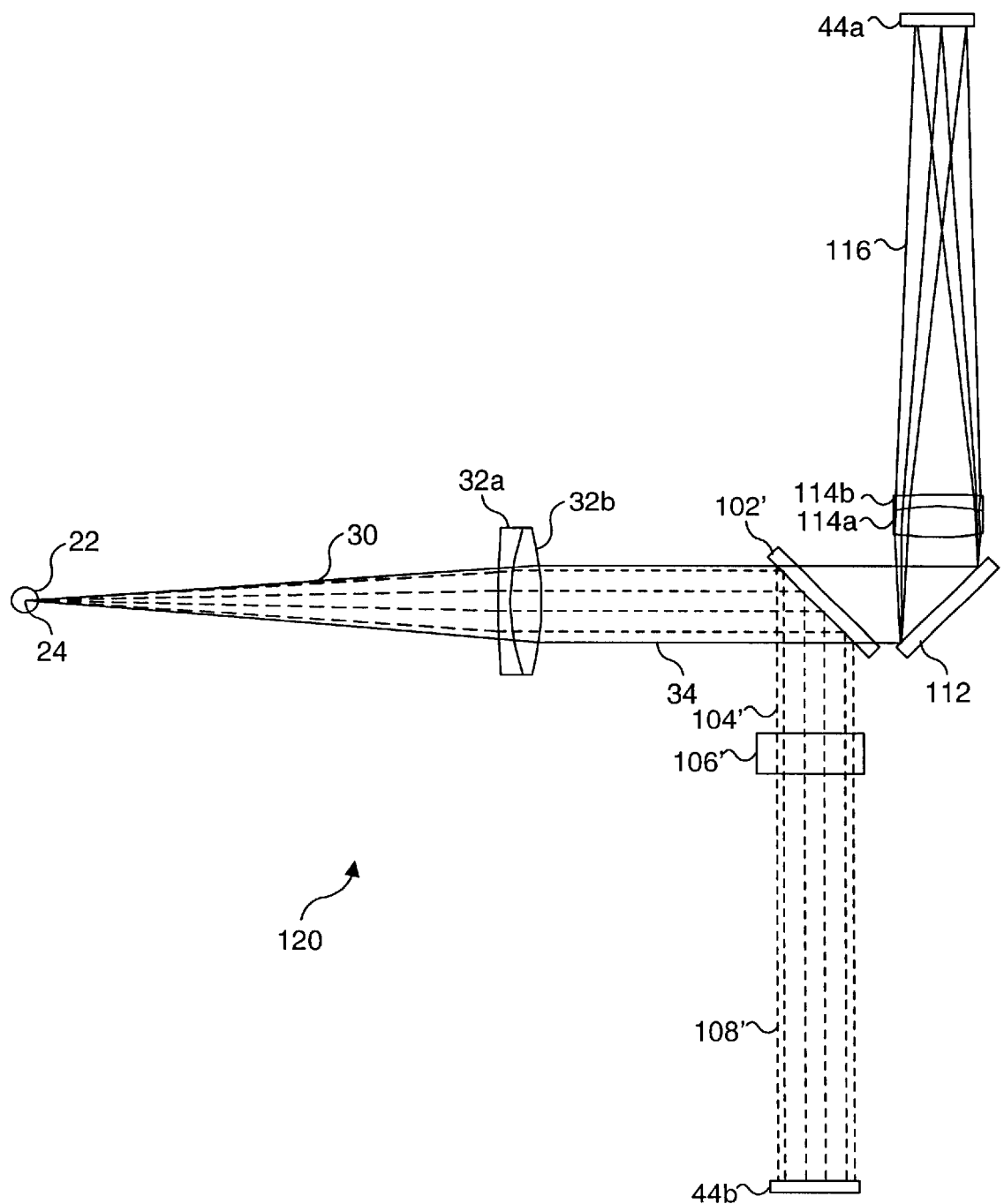
Figure 11:
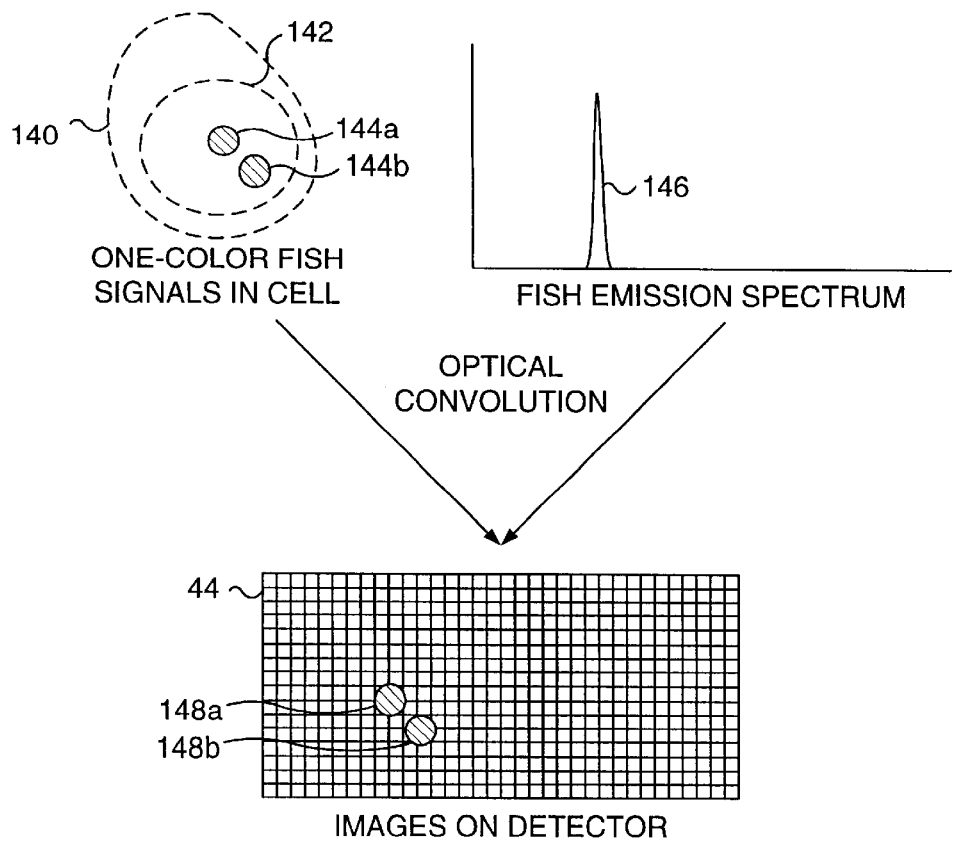
Figure 12:
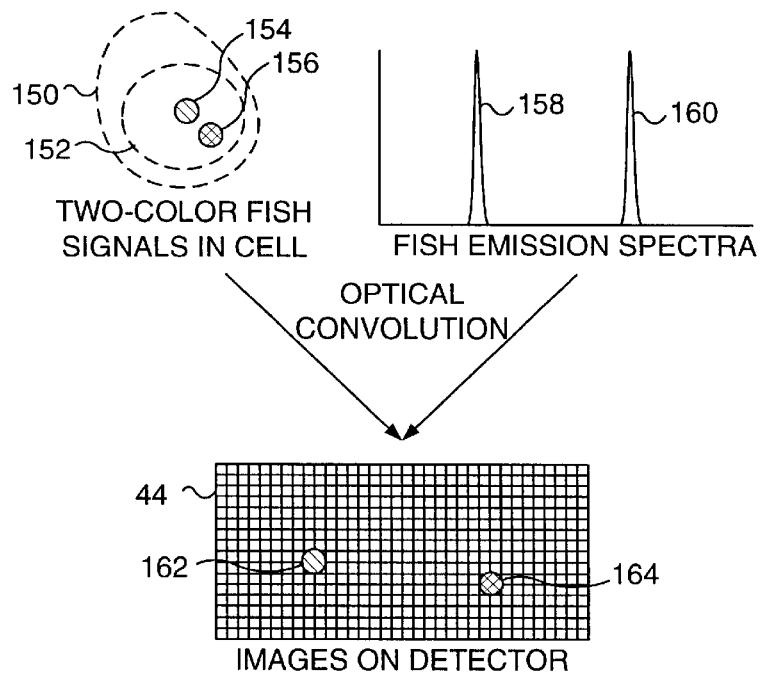
Figure 13:
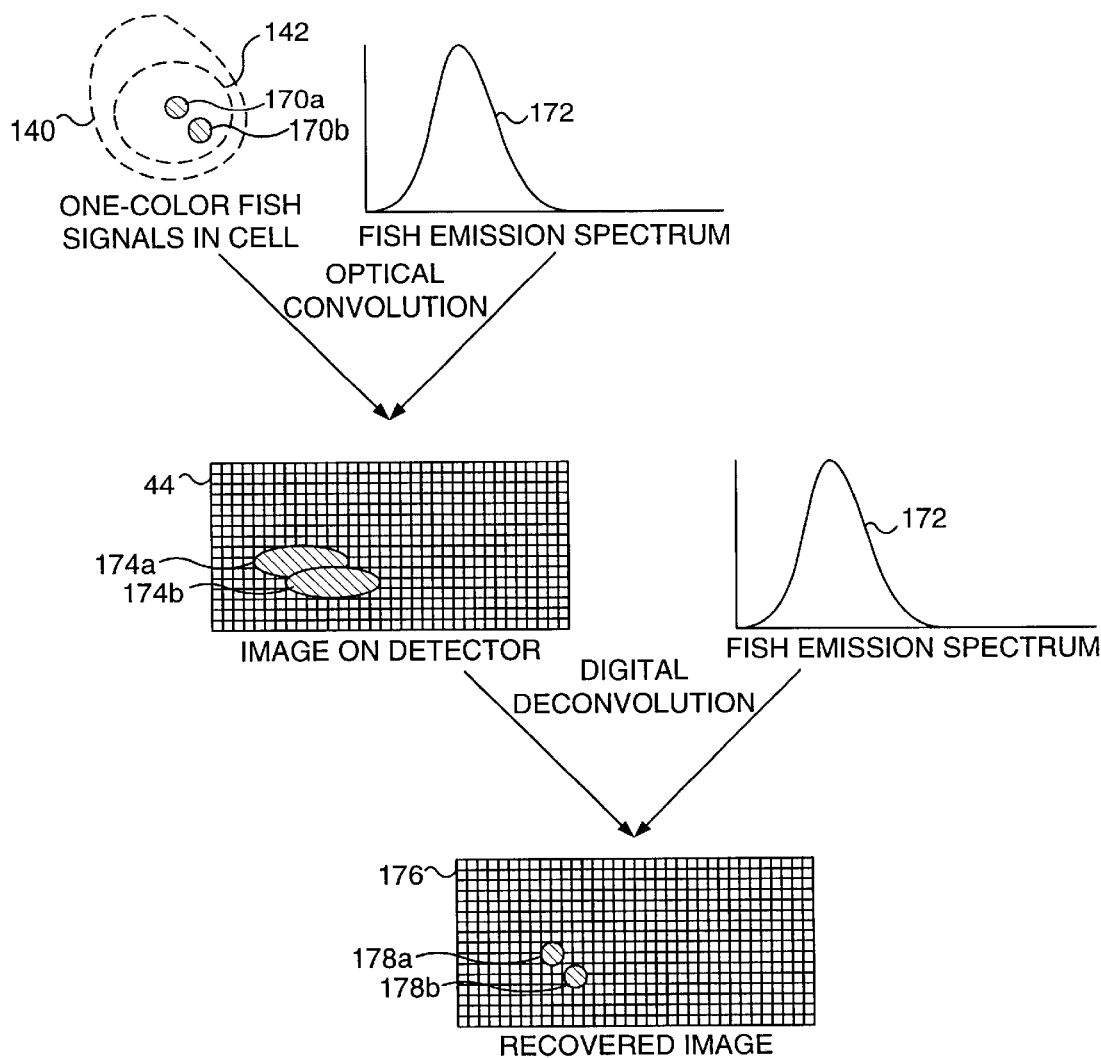
Figure 14:
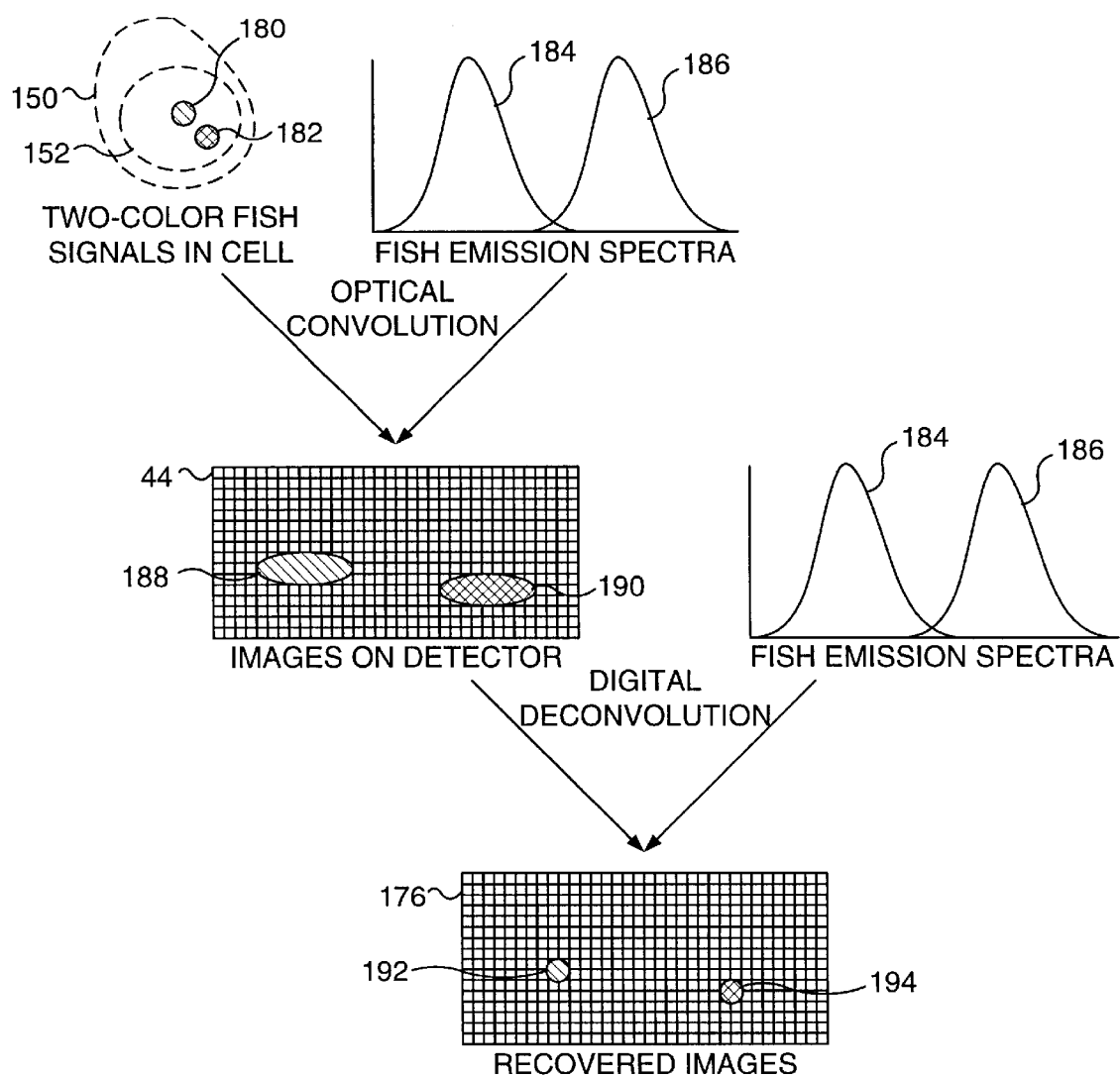
Figure 15:
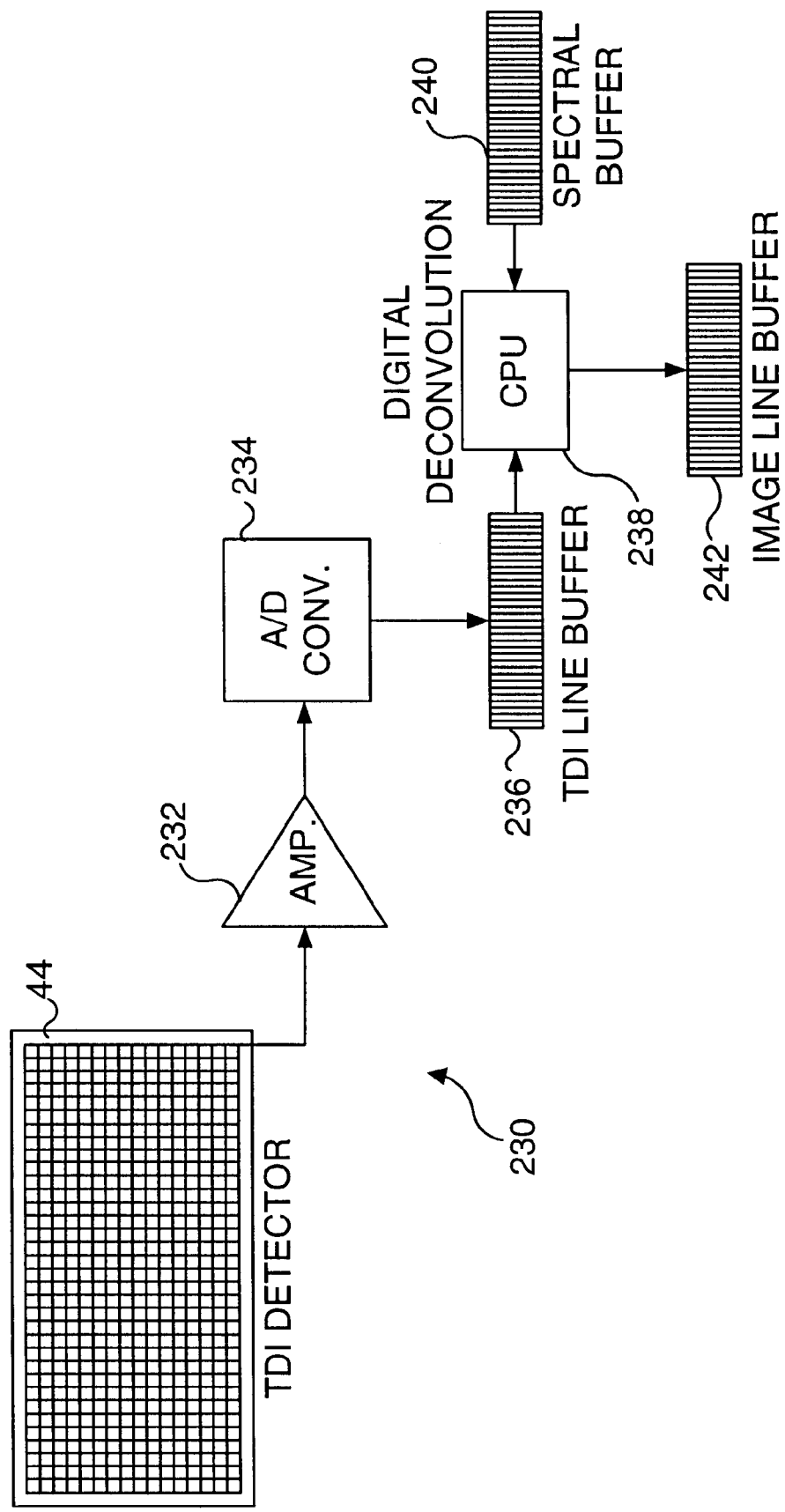
Figure 16:
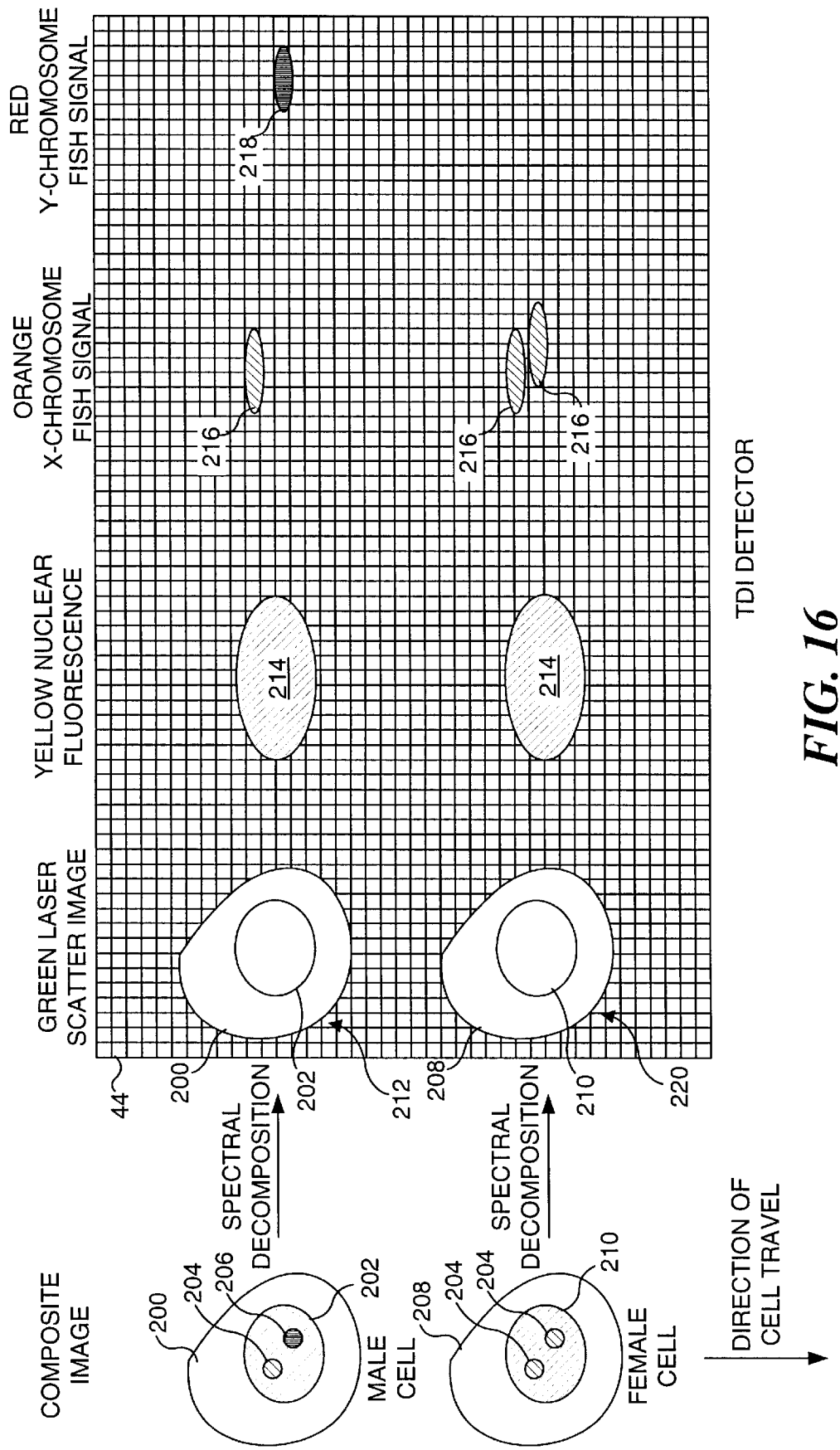

FIG. 6 an alternative to the first embodiment in which a second set of imaging components and TDI detector is included for monitoring light from a particle, to avoid interference between FISH probes, and showing alternative locations for light sources;

FIG. 7 is an isometric view of an embodiment in which an object is supported by or comprises a slide that moves past a collection lens, showing different locations for a light source;

FIGS. 8A and 8B are respectively a plan view and a side elevational view of an alternative to the embodiment of FIG. 7 that is used to produce a scattered pattern on the TDI detector;

FIG. 9 is a plan view of yet a further embodiment in which light forming a scatter patterned image and spectrally dispersed light from the object are imaged on separate portions of a TDI detector;

FIG. 10 is a plan view of a still further embodiment in which light forming a scatter patterned image and spectrally dispersed light from the object are imaged two different TDI detectors;

FIG. 11 is a schematic diagram illustrating the optical convolution of a narrow FISH emission spectrum by the present invention, to resolve two FISH probes in a cell;

FIG. 12 is a schematic diagram showing the optical convolution of two different colors of narrow FISH emission spectra, to resolve the image of the FISH probes on the TDI detector;

FIG. 13 is a schematic diagram illustrating how for a wider FISH emission spectrum, a deconvolution is provided by the present invention to resolve the image of two FISH probes of a single color;

FIG. 14 is a schematic diagram showing the deconvolution of two color FISH spectra that are relatively wide, to resolve the image of the FISH probes;

FIG. 15 is a schematic block diagram of the system used to process the signal produced by a TDI detector in the present invention; and FIG. 16 is a schematic diagram illustrating how the present invention is used to determine whether a cell is from a male or female.

DESCRIPTION OF THE PREFERRED EMBODIMENT

The present invention offers considerable advantages over systems employed for cell and particle analysis in the prior art. These advantages arise from the use in the present invention of an optical dispersion system in combination with a TDI detector that produces an output signal in response to the images of cells and other objects that are directed on the TDI detector. Multiple objects can be imaged on the TDI detector at the same time. In addition, the image of each object can be spectrally decomposed to discriminate object features by absorption, scatter, reflection or probe emissions using a common TDI detector for analysis.

The present invention can be employed to determine morphological, photometric and spectral characteristics of cells and other objects by measuring optical signals including light scatter, reflection, absorption, fluorescence, phosphorescence, luminescence, etc. Morphological parameters include nuclear area, perimeter, texture or spatial frequency content, centroid position, shape (i.e., round, elliptical, barbell-shaped, etc.), volume, and ratios of any of these parameters. Similar parameters can also be determined for the cytoplasm of cells with the present invention. Photometric measurements with the invention enable the determination of nuclear optical density, cytoplasm optical density, background optical density, and the ratios of any of these values. An object being imaged with the present invention can either be stimulated into fluorescence or phosphorescence to emit light, or may be luminescent, producing light without stimulation. In each case, the light from the object is imaged on the TDI detector of the present invention to determine the presence and amplitude of the emitted light, the number of discrete positions in a cell or other object from which the light signal(s) originate(s), the relative placement of the signal sources, and the color (wavelength or waveband) of the light emitted at each position in the object.

An initial application of the imaging system comprising the present invention will likely be employed as a cell analyzer to determine one or more of the parameters listed above, for cells entrained in a fluid flowing through the imaging system. However, it should also be understood that this invention can be used for imaging other moving objects.

First Preferred Embodiment

Figure 1:
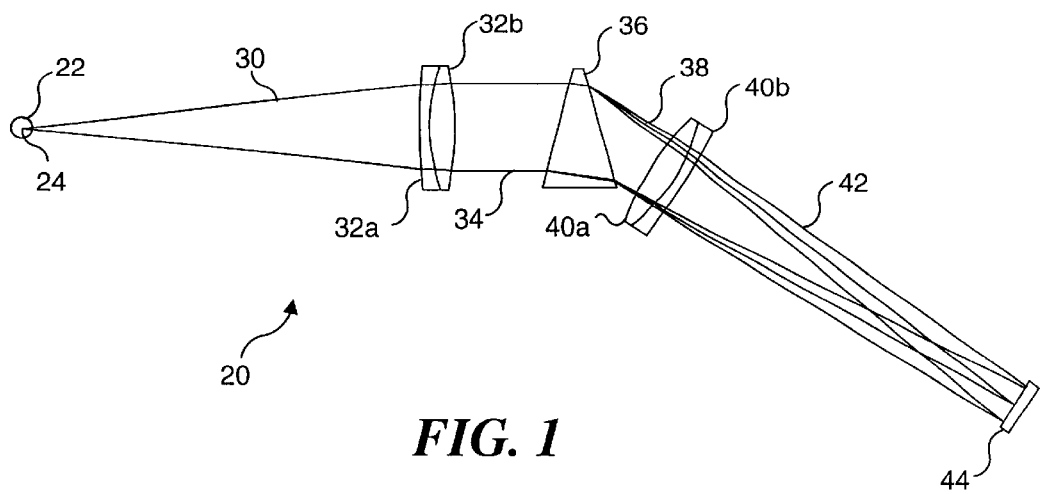
FIG. 1 is a plan view of a first embodiment of the present invention in which particles conveyed by a fluid stream depicted as flowing into the sheet.
Figure 2:
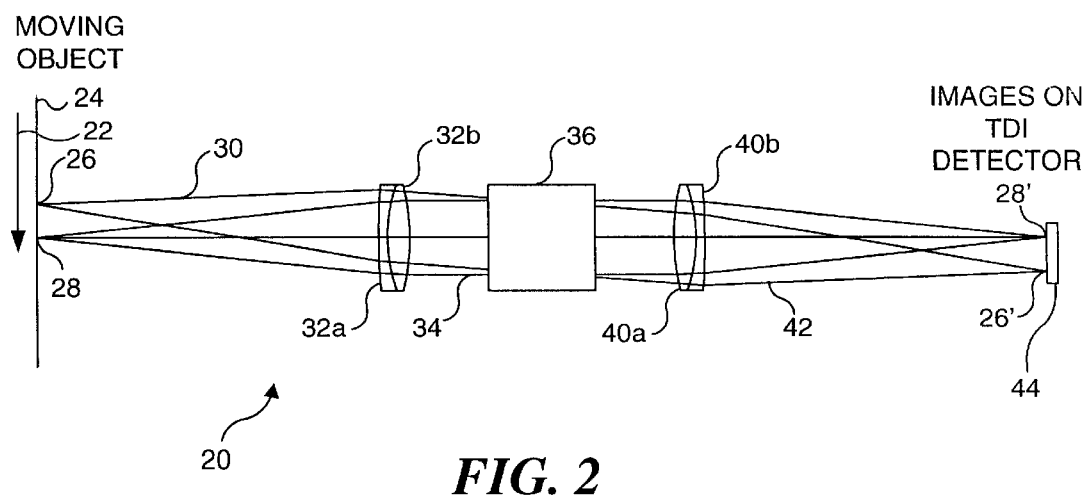
FIG. 2 is a side elevational view of the first embodiment shown in FIG. 1.
Figure 3:
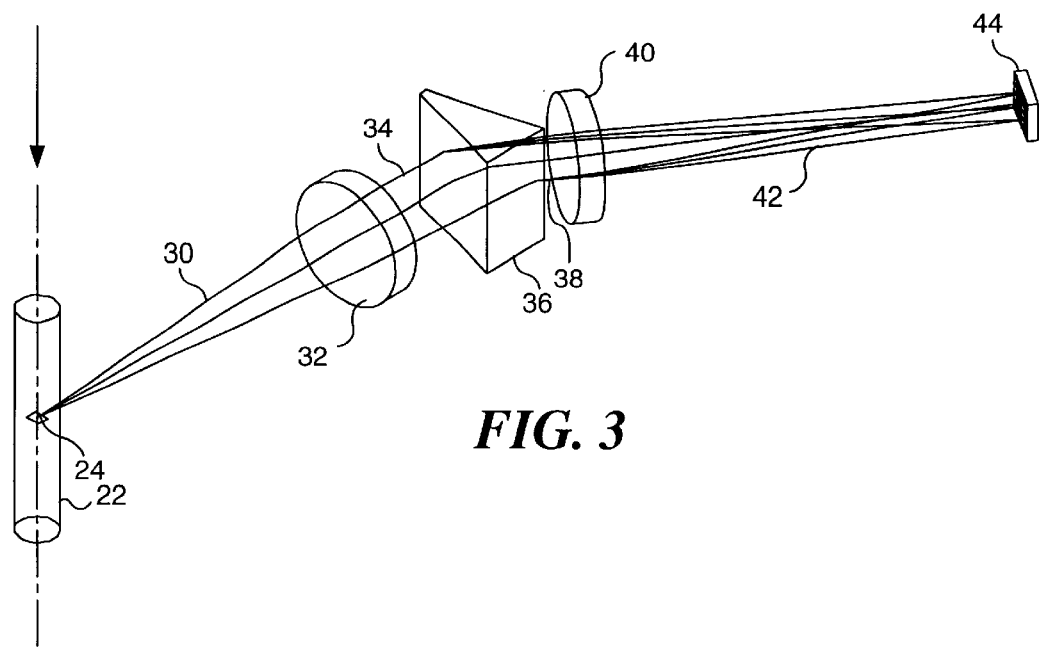
FIG. 3 is an isometric view of the first embodiment of FIG. 1.

A first preferred embodiment of an imaging system 10 in accord with the present invention is schematically illustrated in FIGS. 1, 2, and 3, in connection with producing images of moving objects such as cells that are conveyed by a fluid flow 22 through the imaging system. In FIG. 1, fluid flow 22 entrains an object 24 (such as a cell, but alternatively, a small particle) and carries the object through the imaging system. The direction of the fluid flow in FIG. 1 is into (or out of) the sheet, while in FIGS. 2 and 3, the direction of flow is from top to bottom, as indicated by the arrow to the left of the Figures. Light 30 from object 24 passes through collection lenses 32*a* and 32*b* that collect the light, producing collected light 34, which is approximately focussed at infinity, i.e. the rays of collected light from collection lens 32*b* are generally parallel. Collected light 34 enters a prism 36, which disperses the light, producing dispersed light 38. The dispersed light then enters imaging lenses 40*a* and 40*b*, which focuses light 42 onto a TDI detector 44.

As will be evident in FIG. 2, if the Figure depicts the imaging of object 24 over time, the object is shown at both a position 26 and a position 28 as it moves with fluid flow 22. As a consequence, images of object 24 will be produced on the detector at two discrete spatial positions 26' and 28', as indicated on the right side of FIG. 2. Alternatively, if FIG. 2 is depicting a single instant in time, positions 26 and 28 can represent the location of two separate objects, which are simultaneously imaged on the detector at positions 26' and 28'.

In regard to imaging system 20 and all other imaging systems illustrated herein, it will be understood that the lenses and other optical elements illustrated are shown only in a relatively simple form. Thus, the collection lens is illustrated as a compound lens comprising only collection lenses 32*a* and 32*b*. Lens elements of different designs, either simpler or more complex, could be used in constructing the imaging system to provide the desired optical performance, as will be understood by those of ordinary skill in the art. The actual lenses or optical elements used in the imaging system will depend upon the particular type of imaging application for which the imaging system will be employed.

In each of the embodiments of the present invention, it will be understood that relative movement exists between the object being imaged and the imaging system. In most cases, it will be more convenient to move the object than to move the imaging system. However, it is also contemplated that in some cases, the object may remain stationary and the imaging system move relative to it. As a further alternative, both the imaging system and the object may be in motion but either in different directions or at different rates.

The TDI detector that is used in the various embodiments of the present invention preferably comprises a rectangular charge-coupled device (CCD) that employs a specialized pixel read out algorithm, as explained below. Non-TDI CCD arrays are commonly used for 2-dimensional imaging in cameras. In a standard CCD array, photons that are incident on a pixel produce charges that are trapped in the pixel. The photon charges from each pixel are read out of the detector array by shifting the charges from one pixel to the next, and then onto an output capacitor, producing a voltage proportional to the charge. Between pixel readings, the capacitor is discharged and the process is repeated for every pixel on the chip. During the readout, the array must be shielded from any light exposure to prevent charge generation in the pixels that have not yet been read.

In one type of TDI detector 44, which comprises a CCD array, the CCD array remains exposed to the light as the pixels are read out. The readout occurs one row at a time from the top toward the bottom of the array. Once a first row is read out, the remaining rows are shifted by one pixel in the direction of the row that has just been read. If the object being imaged onto the array moves in synchrony with the motion of the pixels, light from the object is integrated for the duration of the TDI detector's total readout period without image blurring. The signal strength produced by a TDI detector will increase linearly with the integration period, which is proportional to the number of TDI rows, but the noise will increase only as the square root of the integration period, resulting in an overall increase in the signal-to-noise ratio by the square root of the number of rows. One TDI detector suitable for use in the present invention is a Dalsa Corp., Type IL-E2 image sensor, although other equivalent or better image sensors can alternatively be used. The Dalsa image sensor has 96 stages or rows, each comprising 512 pixels; other types of image sensors useable in the present invention may have different configurations of rows and columns or a nonrectilinear arrangement of pixels. The Dalsa sensor has approximately 96 times the sensitivity and nearly 10 times the signal-to-noise ratio of a standard CCD array. The extended integration time associated with TDI detection also serves to average out temporal and spatial illumination variations, increasing measurement consistency.

In imaging system 20 and in other embodiments of the present invention that employ a fluid flow to carry objects through the imaging system, a flowthrough cuvette or a jet (not shown) contains the cells or other objects being analyzed. The velocity and cellular concentration of the fluid may be controlled using syringe pumps, gas pressure, or other pumping methods (not shown) to drive a sample solution through the system to match the pixel readout rate of the TDI detector. However, it should be understood that the readout rate of the TDI detector can be selectively controlled, as required, to match the motion of the sample solution.

Various optical magnifications can be used to achieve a desired resolution of the object that is being imaged on the light sensitive regions (pixels) of the TDI detector. It is contemplated that in most embodiments, the optical magnification will fall within a range of 1:1 to 50:1, providing a substantial range in the number of light sensitive regions on the TDI detector on which images of the object are formed, also depending of course, on the actual size of the object being imaged and its distance from the imaging system. It is envisioned that the present invention can have applications ranging from the analysis of cells and other microscopic objects to the imaging of stellar objects.

It should be emphasized that the present invention is not limited to CCD types of TDI detectors. Other types of TDI detectors, such as complementary metal oxide semiconductor (CMOS) and multi-channel plate imaging devices might also be used for the TDI detector in the present invention. It is important to understand that any pixellated device (i.e., having a multitude of light sensitive regions) in which a signal produced in response to radiation directed at the device can be caused to move through the device in a controlled fashion is suitable for use as the TDI detector in the present invention. Typically, the signal will move in synchrony with a moving image projected onto the device, thereby increasing the integration time for the image, without causing blurring. However, the motion of the signal can be selectively desynchronized from the motion of the radiation image, as required to achieve a desired affect.

Second Preferred Embodiment

Figure 4:
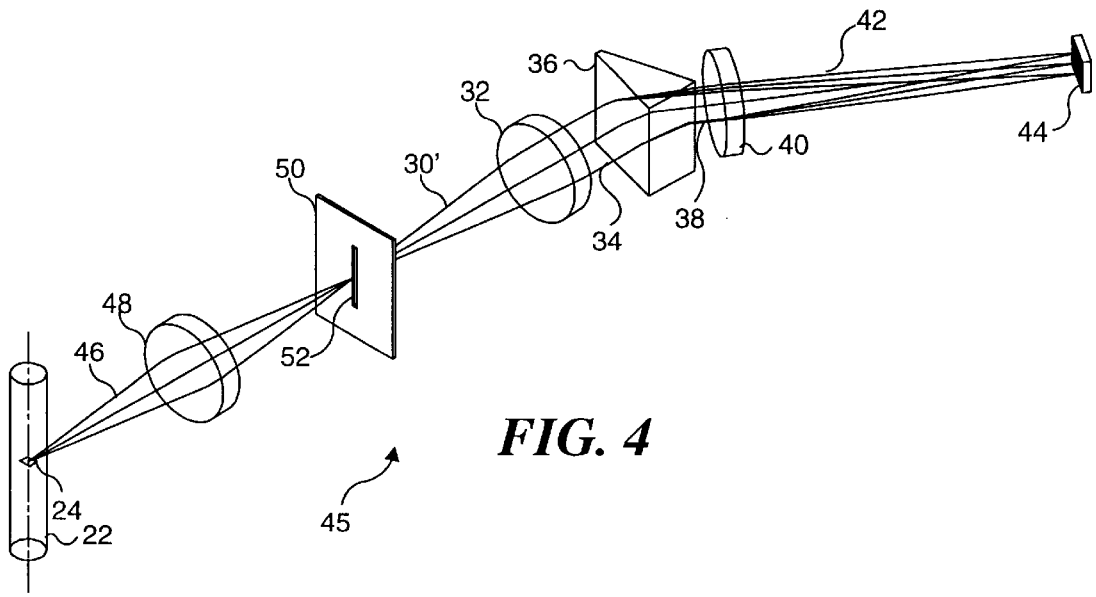
FIG. 4 is an isometric view of a confocal embodiment that includes a slit that is used for spatial filtering of extraneous light.

FIG. 4 illustrates an imaging system 45, which is a second preferred embodiment of the present invention and which is similar in many ways to imaging system 20. However, imaging system 45 is a confocal embodiment that includes a slit 52 that substantially prevents extraneous light from reaching TDI detector 44. In imaging system 45, light 46 from object 24 is focussed by an objective lens 48 onto a slit 52. Slit 52, as shown in FIG. 4, is sufficiently narrow to block light which is not focussed onto the slit by objective lens 48 from passing through the slit. Light 30' passes through the slit and is collected by collection lens 32 as discussed above, in regard to imaging system 20. Collected light 34 is spectrally dispersed by prism 36, and is imaged by imaging lens 40 onto TDI detector 44, also as discussed above. By excluding light other than that from object 24 from reaching TDI detector 44, the TDI detector produces an output signal that corresponds only to the actual images of the object, and the signal is not affected by the extraneous light, which has been excluded. If not excluded in this manner, the ambient light reaching TDI detector 44 might otherwise produce "noise" in the output signal from the TDI detector.

It should be noted that in the illustration of each of imaging systems 20 and 45, a light source has not been shown. These first two embodiments have been illustrated in their most general form to make clear that a separate light source is not required to produce an image of the object, if the object is luminescent, i.e., if the object produces light. However, many of the applications of the present invention will require that one or more light sources be used to provide light that is incident on the object being imaged. The location of the light sources substantially affects the interaction of the incident light with the object and the kind of information that can be obtained from the images on the TDI detector.

Figure 5:
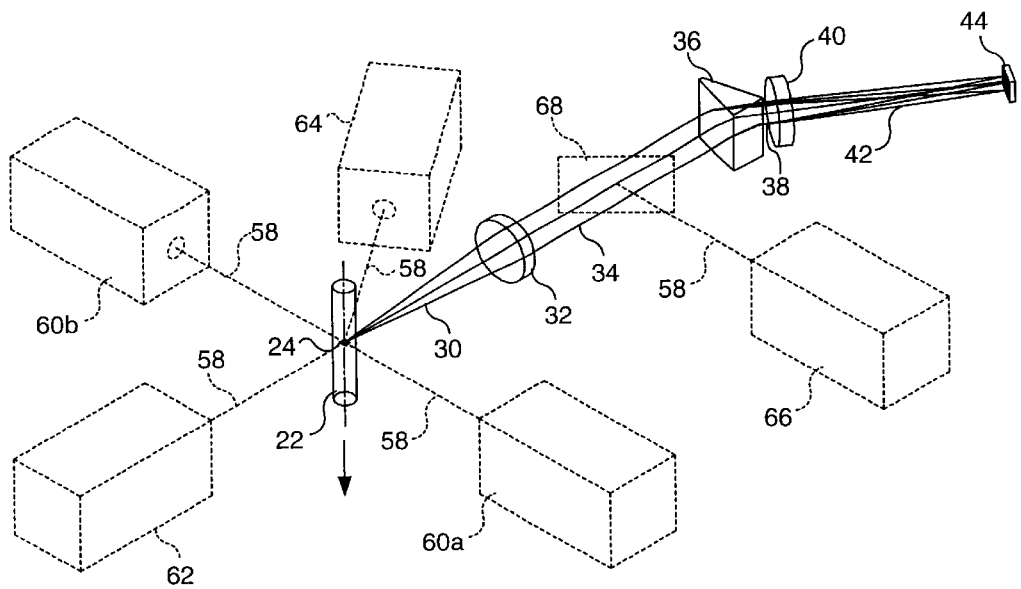
FIG. 5 is an isometric view showing different locations for a light source in connection with the first embodiment.

In FIG. 5, several different locations of light sources usable to provide light incident on object 24 are illustrated. It should be understood, however, that light sources can be located at many other positions besides those shown in FIG. 5. The location of each one or more light source employed will be dependent upon the kind of imaging of the object, and the kind of data for the object, to be derived from the signal produced by the TDI detector. For example, employing a light source 60a or a light source 60b, as shown in the Figure, will provide light 58 that is incident on object 24 and which is scattered from the object into the optical axis of collection lens 32. The optical axis of collection lens 32 is at about a 90° angle relative to the directions of the light incident upon object 24 from either light source 60a or 60b.

In contrast, a light source 62 is disposed so that light 58 emitted from the source travels toward the object in a direction that is generally aligned with the optical axis of collection lens 32, so that the image formed on TDI detector 44 will not include light absorbed by object 24. Light absorption characteristics of the object can thus be determined by illuminating the object using a light source 62.

A light source 64 is disposed to illuminate object 24 with light directed toward the object along a path that is approximately 30–45° off the optical axis of collection lens 32. This light 58, when incident on object 24 will be reflected (scattered) from object 24, and the reflected or scattered light will be imaged on TDI detector 44. A more directly reflected light is provided by an epi light source 66, disposed so as to direct its light 58 toward a partially reflective surface 68 that is disposed so that a portion of the light is reflected through collection lens 32 and onto object 24. The light reaching the object will be reflected from it back along the axis of collection lens 32 and will at least in part pass through partially reflective surface 68 to form an image of the object on TDI detector 44. Alternatively, a dichroic mirror may be employed instead of, and in the position of, partially reflective surface 68 to direct light from epi light source 66 to excite fluorescence or other stimulated emission from object 24. Emission from object 24 is then at least partially collected by collection lens 32 and passes through the dichroic mirror for spectral dispersion and detection by the TDI detector.

In addition to imaging an object with the light that is incident on it, a light source can also be used to stimulate emission of light from the object. For example, FISH probes that have been inserted into cells will fluoresce when excited by light, producing a corresponding characteristic emission spectra from any excited FISH probe that can be imaged on TDI detector 44. In FIG. 5, light sources 60a, 60b, 64, or 66 could alternatively be used for causing the excitation of FISH probes on object 24, enabling TDI detector 44 to image FISH spots produced by the FISH probes on the TDI detector at different locations as a result of the spectral dispersion of the light from the object that is provided by prism 36. The disposition of these FISH spots on the TDI detector surface will depend upon their emission spectra and their location in the object. Use of FISH probes in connection with producing images of FISH spots on the TDI detector with the present invention is discussed in greater detail below.

Each of the light sources illustrated in FIG. 5 produces light 58, which can either be coherent, non-coherent, broadband or narrowband light, depending upon the application of the imaging system desired. Thus, a tungsten filament light source can be used for applications in which a narrowband light source is not required. For applications such as stimulating the emission of fluorescence from FISH probes, narrowband laser light is preferred, since it also enables a spectrallydecomposed, non-distorted image of the object to be produced from light scattered by the object. This scattered light image will be separately resolved from the FISH spots produced on TDI detector 44, so long as the emission spectra of any FISH spots are at different wavelengths than the wavelength of the laser light. The light source can be either of the continuous wave (CW) or pulsed type. If a pulsed type illumination source is employed, the extended integration period associated with TDI detection can allow the integration of signal from multiple pulses. Furthermore, it is not necessary for the light to be pulsed in synchronization with the TDI detector.

Pulsed lasers offer several advantages over CW lasers as a light source in the present invention, including smaller size, higher efficiency, higher reliability, and the ability to deliver numerous wavelengths simultaneously. Another advantage of pulsed lasers is their ability to achieve saturating levels of fluorescence excitation of fluorescent probes used in cells. Fluorescence saturation occurs when the number of photons encountering a fluorescent molecule exceeds its absorption capacity. Saturating excitation produced by a pulsed laser is inherently less noisy than unsaturating CW laser excitation because variations in pulse-to-pulse excitation intensity have little effect on the fluorescence emission intensity.

Prism 36 in the imaging systems discussed above can be replaced with a diffraction grating, since either is capable of spectrally dispersing the optical signals from the cells over the pixels of the TDI detector. In addition to providing useful data from a cell or other object, spectral dispersion can be used to reduce measurement noise. In cases where the light source wavelength differs from the emission spectra of the fluorescent probes, the light from the source that is scattered into the collection system is spatially isolated from the fluorescence signals. If the light source wavelength overlaps the emission spectra of the fluorescent probes, the pixels of the TDI detector in which light of the wavelength of the source falls can be isolated from those pixels on which the remaining fluorescence signals fall. Further, by dispersing the fluorescence signals over multiple pixels, the overall dynamic range of the imaging system is increased.

Third Preferred Embodiment

A third preferred embodiment is a stereoscopic arrangement of the first preferred embodiment, as illustrated in FIG. 6. This arrangement allows the imaging of the object from two different directions in order to distinguish features that would otherwise overlap when viewed from a single direction. While preferred embodiment 3 can be employed for objects on moving substrates such as microscope slides, it is particularly useful for analyzing multi-component objects in solution, such as cells containing FISH probes. Such probes appear as point sources of light anywhere within the cell's three dimensional nucleus. In some cases, two or more FISH probes may appear in an overlapping relationship along the optical axis of the imaging system. In such cases, one of the FISH probes may obscure the others, making it difficult to determine the number of probes present in the cell. This is a key factor in the determination of genetic abnormalities such as trisomy 21, otherwise known as Down syndrome. Single-perspective systems may address this problem by "panning through" the object along the optical axis to acquire multiple image planes in the object. While this method may be effective, it requires a significant amount of time to collect multiple images and cannot be readily applied to a cell in flow. The stereoscopic imaging system 70 in FIG. 6 includes two TDI detectors 44a and 44b, and their associated optical components, as discussed above in connection with imaging system 20.

By positioning the optical axes of collection lenses 32 for the two TDI detectors so that they are spaced apart, for example, by 90°, it is possible to separately resolve the FISH spots imaged from two or more FISH probes on at least one of TDI detectors 44a or 44b. If two or more FISH probes overlap in regard to the image produced on one of the detectors, they will be separately resolved in the spectrally dispersed images produced on the other TDI detector. Further, the use of two TDI detectors in imaging system 70 in what might be referred to as a "stereo or three-dimensional configuration" allows flexibility in the configuration of each leg of the system, including parameters such as the relative TDI readout rates, axial orientations, inclinations, focal plane positions and magnification. Multiple cells or other objects may be imaged onto each detector simultaneously in the vertical direction. Since the objects may move in synchronicity with the signal on the TDI, no gate or shutter is required to prevent blurring of the image. As previously noted, the present invention can use a pulsed or CW light source without need for a trigger mechanism to time a pulse coincident with particle arrival in the field of view. If a pulsed light source is used, the extended field of view in the axis of motion associated with TDI detection allows the cell or object in motion to be illuminated by multiple pulses during its traversal. In contrast to a frame-based imaging apparatus, a TDI system can produce a single unblurred image of the object that integrates the signal from multiple pulses. When a CW light source is used, the signal generated by the object will be collected throughout the entire traversal of the object through the field of view, as opposed to only a small segment in time when a shutter is open. Therefore, the amount of signal collected and imaged on the detector in the present invention is substantially greater than that of the prior art frame-based imaging systems. Consequently, the present invention can operate at very high throughput rates with excellent signal to noise ratio.

Also illustrated in FIG. 6 are several exemplary positions for light sources, which are useful for different purposes in connection with the imaging system illustrated therein. In connection with TDI detector 44a, light source 62 provides illumination of object 24 from a direction so that absorption characteristics of the object can be determined from the image produced on the TDI detector. At the same time, light provided by light source 62 that is scattered from object 24 can be used to produce a scatter image and spectrally dispersed images on TDI detector 44b. Light source 74 can be employed to produce spectrally dispersed and scattered images on both TDI detectors 44a and 44b. If light sources 62 and 72 are of different wavelengths and an appropriate filter is provided to block the wavelength from the light source aligned with the optical axis of the respective collections lenses 32, these two light sources can be used for producing scattered light from the object. For example, suppose light source 72 produces light of a wavelength A that scatters from object 24 and is directed toward TDI detector 44a. By including a filter (not shown) that blocks wavelength B produced by light source 62, the light at wavelength B will not directly affect the images produced on TDI detector 44a. Similarly, the light from light source 72 would be blocked with an appropriate filter (not shown) so that it does not interfere with the imaging of light produced by light source 62 that is scattered from object 24 onto TDI detector 44b.

Epi light source 66 is also illustrated for use in producing images on TDI detector 44a in conjunction with partial reflector 68. Light source 64 can be used to generate reflected light to produce images on TDI detector 44a, while scattered light from this source is directed toward TDI detector 44b. These and other possible locations of light sources will be apparent to those of ordinary skill in the art, as appropriate for providing the incident light on the object needed to achieve imaging, depending upon the particular application and information about the object that is desired.

Imaging Slide or Object Carried by Slide

Turning now to FIG. 7, an imaging system 80 is illustrated that is similar to imaging system 20, except that it is used for imaging object 24 on a slide 82. Object 24 is supported by slide 82 and the slide moves relative to the imaging system as shown in FIG. 7. Alternatively, slide 82 may be the object that is imaged. The object may be a semiconductor wafer, paper, or other object of interest since the object may be imaged using reflected incident light.

To provide light incident on either slide 82 or object 24 that is supported thereby, a light source placed at one of several different locations can be employed. Exemplary light sources 62, 64, and 66 illustrate some of the locations at which light sources useful in this embodiment may be disposed. Light 58 emitted by any of the light sources can be either coherent or non-coherent light, pulsed or CW, and can be directed through slide 82 (if it is transparent) from light source 62 or can be reflected from the object or slide, if light sources 64 or 66 are employed. As noted previously, epi light source 66 illuminates the object in connection with a partially reflective surface 68.

Fourth Preferred Embodiment

FIGS. 8A and 8B show two different views of a fourth preferred embodiment, which is an imaging system 90 that produces a scattered pattern image of object 24 on TDI detector 44. Light 30 from object 24 passes through collection lenses 32a and 32b, and collected light 34 is directed onto a cylindrical lens 92, as in the previous embodiments. Cylindrical lens 92 focuses light 94 on TDI detector 44, generally along a line that is aligned with a central axis 96 of cylindrical lens 92. Central axis 96 is shown in FIG. 8B, and it will be apparent that it is orthogonal to the direction in which object 24 moves through the imaging system. As object 24 moves downwardly, relative to its disposition as shown in FIG. 8A, the focus of cylindrical lens 92 on TDI detector 44 moves upwardly. Cylindrical lens 92 thus distributes an image of the object along a row or rows of the light sensitive regions or pixels of TDI detector 44.

Fifth Preferred Embodiment

Referring now to FIG. 9, an illustration of a fifth preferred embodiment is provided of an imaging system 100 that produces both a scattered pattern image and a spectrally dispersed image of object 24 on TDI detector 44. In imaging system 100, light 30 from object 24 passes through collections lenses 32a and 32b, which produce infinitely focussed light 34 directed toward a dichroic filter 102. Dichroic filter 102 reflects light of a specific wavelength, e.g., the wavelength of a light source (not shown) that is incident upon object 24. Light of any other wavelength is transmitted through dichroic filter 102 toward a diffraction grating 112. Diffraction grating 112 spectrally disperses the light transmitted through dichroic filter 102, which typically would be light produced by the fluorescence of FISH probes on object 24, so that a plurality of FISH spots corresponding to the number of different FISH probes and objects being imaged are produced on TDI detector 44.

Light 104, which is reflected from dichroic filter 102 is transmitted into cylindrical lens 106 and is focussed along a line as a scattered pattern image in a region 110 on the TDI detector. The spectrally dispersed images of FISH spots or other aspects of object 24 having wavelengths different than that reflected by dichroic filter 102 are imaged as light 116 by imaging lenses 114a and 114b onto a region 118 of the TDI detector. Thus, signals corresponding to the scattered pattern image and the spectrally dispersed images are both produced by TDI detector 44.

Sixth Preferred Embodiment

A sixth preferred embodiment, as illustrated in FIG. 10, is an imaging system 120 that is slightly different than the preceding fifth embodiment, since a dichroic filter 102' is employed that is angled in a different direction, toward a second TDI detector 44b. A dispersed pattern image represented by light 108' is produced by a cylindrical lens 106' in this embodiment. Just as in imaging system 100, light transmitted through dichroic filter 102' is focussed onto TDI detector 44a. Aside from using two separate TDI detectors that are disposed at different sides of the imaging system, imaging system 120 is substantially identical in operation to imaging system 100. However, just as in the third preferred embodiment, the use of two separate TDI detectors allows flexibility in the configuration of each leg of the system, including parameters such as the relative TDI readout rates, axial orientations, inclinations, focal plane positions, and magnification. It should also be noted that imaging system 100 could be constructed to include two separate TDI detectors instead of a single TDI detector, if desired.

Processing of Spectrally Dispersed Images on TDI Detector

When used for cell analysis, the present invention provides substantial utility in resolving FISH spots on the TDI detector, even when the FISH probes are disposed in spatially close relationship within the cell. When spectral imaging occurs in the present invention, the spatial distribution of light in the object is convolved with the spectral distribution of that light to produce the image of the object at the TDI detector. This convolution can result in blurring in the dispersion axis, depending on the spectral bandwidth of the light. Narrow spectral bandwidths will result in little or no blurring depending on the spectral resolution of the system. In the present invention, it is contemplated that the spectral resolution will be approximately 3 nm per pixel, with a spatial resolution in object space of approximately 1 micron. However, the spatial and spectral resolution can be adjusted to match the requirements of the particular application.

FIG. 11 illustrates the present invention with a spectral resolution of approximately 10 nm per pixel and a spatial resolution of approximately 0.5 microns. This Figure further illustrates how the present invention is used to image a cell 140 having a nucleus 142 in which are disposed two FISH probes 144a and 144b having the same emission spectrum. In FIG. 11, the emission spectrum 146 of the FISH probes 144a and 144b is approximately 10 nm in width, such as would be produced by "quantum dots" or a narrow-band fluorescent dye. The optical convolution of the narrow bandwidth spectrum results in minimal blurring of FISH spots 148a and 148b, enabling them to be readily resolved on TDI detector 44.

In FIG. 12, a cell 150 is illustrated having a nucleus 152 in which are disposed FISH probes 154 and 156 having different emission spectra. FISH probes are designed so that different emission spectra correspond to different DNA sequences. Each of the emission spectra of FISH probes 154 and 156 are relatively narrow, as indicated by wavebands 158 and 160, and therefore, as in FIG. 11, minimal blurring occurs in FISH spots 162 and 164. Furthermore, the spectral dispersion of the present invention, which maps wavelength into lateral position on TDI detector 44, produces a relatively wide physical displacement of FISH spots 162 and 164, despite the close proximity of FISH probes 154 and 156 in the cell. Taken together, FIGS. 11 and 12 illustrate how the present invention discriminates FISH probes of the same or different color, thereby enabling the simultaneous enumeration of numerous genetic traits. Those skilled in the art can appreciate that the present invention is well suited to the requirements of fetal cell analysis, where there may be ten or more probes of different colors present in the cell at one time. Further, those skilled in the art will appreciate that the present invention is not limited to the analysis of fetal cells using FISH probes.

FIGS. 13 and 14 illustrate that the present invention can also be used with light of wide spectral bandwidth. In this case an additional signal processing step is performed to correct for lateral blurring due to the wide emission spectra. In FIG. 13, a cell 140 having a nucleus 142 is shown, and FISH probes 170a and 170b having a common emission spectrum are disposed in the nucleus. FISH probes 170a and 170b are characterized by producing a relatively wide emission spectrum 172. When optically convolved by the spectral dispersion provided by the present invention, FISH spots 174a and 174b are produced on TDI detector 44, but their images are laterally blurred across TDI detector 44, as a result of their relatively wide emission spectrum. To more clearly resolve the separation of FISH spots probes 174a and 174b, a deconvolution is carried out on the signal produced by TDI detector 44, with the known FISH emission spectrum, thereby producing accurate FISH spot representations 178a and 178b on a display 176. The deconvolution step enhances the ability to enumerate the number of FISH spots.

FIG. 14 illustrates a corresponding relationship between FISH probes 180 and 182, which are disposed within a nucleus 152 of a cell 150. FISH probes 180 and 182 are characterized by each producing relatively wide band emission spectra 184 and 186, as shown in the Figure. Optical convolution of the fluorescence emitted by the FISH probes, which are spectrally dispersed, produces FISH spots 188 and 190 on TDI detector 44. Again, by deconvolving the known FISH emission spectra with the signal produced by TDI detector 44, the corresponding images shown on display 176 of FISH spots 192 and 194 are recovered. Again, the spectral dispersion of the present invention, which maps wavelength into lateral position on TDI detector 44, produces a relatively wide physical displacement of FISH spots 192 and 194, despite the close proximity of FISH probes 180 and 182 in the cell. In this manner, it is possible to resolve these images of FISH spots produced by FISH probes having different and relatively wide emission spectra.

A system 230 for analyzing the signal produced by TDI detector 44 and performing the deconvolution steps described above is illustrated in FIG. 15. In this Figure, the signal from TDI detector 44 is applied to an amplifier 232, which buffers the signal and amplifies it to achieve a level required by an analog to digital (A-D) converter 234. This A-D converter converts the analog signal from amplifier 232 into a digital signal that is input into a TDI line buffer 236. TDI line buffer 236 temporarily stores the digital signal until it can be processed by a CPU 238. To carry out the deconvolution noted above, a spectral buffer 230 is loaded with the known emission spectrum for each of the FISH probes being used so that their emission spectra can be deconvolved with the signal stored in TDI line buffer 236. CPU 238 is a high speed processor programmed to carry out the deconvolution and other analysis procedures, enabling the identification of desired characteristics or parameters of the object being imaged. The output from CPU 238 is temporarily stored in an image line buffer 242 that enables the image to be displayed or otherwise recorded for later analysis.

FIG. 16 illustrates a practical application of the present invention for identifying a male cell 200 and a female cell 208 and for producing their corresponding scatter images 212 and 220. Male cell 200 includes a nucleus 202 that has been stained with a yellow fluorescent dye. In addition, a FISH probe 204 produces a fluorescent orange emission, indicating the presence of an X-chromosome in the nucleus, while a FISH probe 206 produces red fluorescence emission, indicating the presence of a Y-chromosome. Spectral decomposition of the fluorescence emissions from male cell 200, when the cell is illuminated with light from a green laser, results in a series of images on TDI detector 44, separated as a function of the wavelength of the light that is imaged. Laser light that is incident on the cells has an extremely narrow waveband, and image 212 of male cell 200 produced by laser scatter is only slightly convoluted by the spectral decomposition process. Green laser scatter image 212 of cell 200 and its nucleus 202 appear on the left side of the TDI detector, while a fluorescent spot 214 corresponding to the yellow fluorescence emitted by nucleus 202 appears in the next few columns on the TDI detector. Furthermore, as a function of the different wavelengths of the fluorescence emitted by FISH probes 204 and 206, FISH spots 216 and 218 appear at locations spaced apart on the detector, but slightly blurred across the columns of TDI detector 44 due to the widths of their respective emission spectra. By analyzing the signals produced by the TDI detector, the FISH probes responsive to X and Y chromosomes arc detected, enabling the user to determine that cell 200 is a male cell, since it includes both the X and Y chromosome. Similarly, female cell 208, when spectrally decomposed, also includes the characteristic yellow fluorescence of nucleus 210, but unlike the male cell, includes two FISH spots 216 corresponding to FISH probes 204, which indicates the presence of two X-chromosomes. Because TDI detector 44 also distinguishes the spatial position of male cell 200 and female cell 208, the corresponding spectral decompositions for these cells are readily separately resolved as both cells pass through the imaging system in the direction indicated by the arrow to the lower left of FIG. 16. Again, it should be noted that a deconvolution can be applied to the signal produced by TDI detector 44 to provide better resolution of the corresponding FISH spots that are illustrated.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. An imaging system adapted to determine one or more characteristics of an object from an image of the object in which at least one component of the object is detected while there is relative movement between the object and the imaging system, comprising:
   (a) a collection lens disposed so that light traveling from the object passes through the collection lens and travels along a collection path, said collection lens substantially collimating light from the object;
   (b) a light dispersing element disposed in the collection path so as to disperse the light that has passed through the collection lens, producing dispersed light;
   (c) an imaging lens disposed to receive the dispersed light, producing an image from the dispersed light; and
   (d) a time delay integration (TDI) detector disposed to receive the image produced by the imaging lens, said image clearly separately distinguishing components included in the object, producing an output signal that is indicative of at least one characteristic of the object, said TDI detector producing the output signal by integrating light from at least a portion of the object over time, while the relative movement between the object and the imaging system occurs.

2. The imaging system of claim 1, wherein the light dispersing element spectrally disperses the light that has passed through the collection lens, and wherein the dispersed light is spectrally dispersed across the TDI detector.

3. The imaging system of claim 1, wherein the light that has passed through the collection lens is dispersed in a plane that is orthogonal to a direction of the relative movement between the object and the imaging system.

4. The imaging system of claim 1, wherein the image of the object produced by the imaging lens moves across the TDI detector as the relative movement between the object and the imaging system occurs.

5. The imaging system of claim 1, wherein the light from the object comprises an unstimulated emission from the object.

6. The imaging system of claim 1, further comprising a light source that is disposed to provide an incident light that illuminates the object.

7. The imaging system of claim 6, wherein the object scatters the incident light, said light that is scattered from the object at least in part passing through the collection lens.

8. The imaging system of claim 6, wherein the incident light illuminating the object stimulates the object to emit the light that passes through the collection lens.

9. The imaging system of claim 6, wherein the incident light is at least partially absorbed by the object, so that the light passing through the collection lens does not include a portion of the light absorbed by the object.

10. The imaging system of claim 6, wherein the incident light is reflected from the object toward the collection lens.

11. The imaging system of claim 6, wherein the light source comprises at least one of:
    (a) a coherent light source;
    (b) a non-coherent light source;
    (c) a pulsed light source; and
    (d) a continuous light source.

12. The imaging system of claim 1, wherein the object is entrained within a fluid stream that moves the object past the collection lens.

13. The imaging system of claim 1, wherein the object is carried on a support past the collection lens.

14. The imaging system of claim 1, wherein the TDI detector responds to the image of the object by producing a signal that propagates through the TDI detector.

15. The imaging system of claim 14, wherein a propagation rate of the signal through the TDI detector is synchronized with a motion of the image of the object on the TDI detector as a result of the relative movement between the object and the imaging system.

16. The imaging system of claim 14, wherein a propagation rate of the signal through the TDI detector is not synchronized with a motion of the image of the object on the TDI detector as a result of the relative movement between the object and the imaging system.

17. The imaging system of claim 1, wherein the dispersing element comprises a prism.

18. The imaging system of claim 1, further comprising an objective lens disposed between the object and the collection lens, having a focal point at which the object is imaged; and an optical slit aligned with a direction of the relative movement between the object and the imaging system and disposed between the objective lens and the collection lens at the focal point of the objective lens, said slit substantially preventing extraneous light reaching the collection lens by transmitting to the collection lens the light from the object that is focussed on the slit by the objective lens.

19. An imaging system adapted to determine one or more characteristics of an object from a scatter pattern image of the object while there is relative movement between the object and the imaging system, comprising:
    (a) a light source that produces light incident on the object;
    (b) a collection lens disposed so that light emitted by the light source and traveling from the object passes through the collection lens and travels along a collection path, said collection lens having a focal plane that is conjugate to the object;
    (c) a cylindrical lens disposed in the collection path to receive the light that has passed through the collection lens from the object, said cylindrical lens having a central axis around which the cylindrical lens is curved, said central axis being generally orthogonal to a direction of the relative movement between the object and the imaging system, so that the cylindrical lens produces a scattered pattern image of the object along a direction that is substantially parallel to said central axis of the cylindrical lens; and
    (d) a time delay integration (TDI) detector disposed to receive the scattered pattern image produced by the cylindrical lens, producing an output signal that is indicative of at least one characteristic of the object, said TDI detector producing the output signal by integrating light from at least a portion of the object over time.

20. The imaging system of claim 19, wherein the TDI detector includes a plurality of light sensitive regions arranged in an array of rows and columns, said scattered pattern image being distributed along either a row or a column of the light sensitive regions, said array being oriented with either the rows or the columns of the array aligned with the central axis of the cylindrical lens.

21. The imaging system of claim 19, wherein light emitted by the light source illuminates a plurality of objects so that the light from the plurality of objects passes through the collection lens and the cylindrical lens, forming a plurality of separate scattered pattern images on the TDI detector, the signals produced by the TDI detector in response to the separate scattered pattern images indicating at least one characteristic of each of the plurality of objects.

22. The imaging system of claim 19, wherein the object is entrained within a fluid stream that moves the object past the collection lens.

23. The imaging system of claim 19, wherein a signal propagates through the TDI detector, and wherein a propagation rate of said signal through the TDI detector is synchronized with a motion of the scattered pattern image of the object on the TDI detector caused by the relative movement of the object relative to the imaging system.

24. The imaging system of claim 19, wherein a signal propagates through the TDI detector, and wherein a propagation rate of the signal through the TDI detector is not synchronized with a motion of the scattered pattern image of the object on the TDI detector caused by the relative movement of the object relative to the imaging system.

25. The imaging system of claim 19, wherein the object is carried on a support that moves the object past the collection lens.

26. The imaging system of claim 19, wherein the light source comprises at least one of:
   (a) a coherent light source;
   (b) a non-coherent light source;
   (c) a pulsed light source; and
   (d) a continuous light source.

27. The imaging system of claim 19, wherein the scattered pattern image is distributed along the TDI detector along a line that is aligned with the central axis of the cylindrical lens, said line moving across the TDI detector in accord with the relative movement between the object and the imaging system.

28. An imaging system adapted to determine different characteristics of an object from images of the object in which components of the object are detected while there is relative movement between the object and the imaging system, comprising:
   (a) a first collection lens disposed so that light from the object passes through the first collection lens and travels along a first collection path, said first collection lens substantially collimating the light traveling along the first collection path;
   (b) a first light dispersing element disposed in the first collection path so as to disperse the light that has passed through the first collection lens, producing first dispersed light;
   (c) a first imaging lens disposed to receive the first dispersed light, producing at least one image from the first dispersed light;
   (d) a first time delay integration (TDI) detector disposed to receive said at least one image produced by the first imaging lens, said at least one image clearly separately distinguishing components included in the object, producing a first output signal that is indicative of at least one characteristic of the object, said first TDI detector producing the first output signal by integrating the first dispersed light from at least a portion of the object over time, while the relative movement between the object and the imaging system occurs;
   (e) a second collection lens disposed so that light from the object passes through the second collection lens and travels along a second collection path different than the first collection path, said second collection lens substantially collimating the light traveling along the second collection path;
   (f) a second light dispersing element disposed in the second collection path so as to disperse the light that has passed through the second collection lens, producing second dispersed light;
   (g) a second imaging lens disposed to receive the second dispersed light from the second light dispersing element, producing at least one image from said second dispersed light; and
   (h) a second TDI detector disposed to receive said at least one image produced by the second imaging lens, said at least one image clearly separately distinguishing components included in the object, producing a second output signal that is indicative of at least one other characteristic of the moving object, said second TDI detector producing the second output signal by integrating the second dispersed light from at least a portion of the object over time while the relative movement between the object and the imaging system occurs, said first and second output signals being indicative of substantially different characteristics of the moving object.

29. The imaging system of claim 28, further comprising a light source that produces light incident on the object, wherein the light from the object includes an emission from the object stimulated by the light from the light source that is incident on the object.

30. The imaging system of claim 28, wherein the object is entrained within a fluid stream that moves the object past the first and the second collection lens to achieve the relative movement between the object and the imaging system.

31. The imaging system of claim 28, wherein the object is carried on a support.

32. An imaging system adapted to determine characteristics of an object from images of the object, while there is relative movement between the object and the imaging system, comprising:
   (a) a light source that emits light incident on the object;
   (b) a collection lens disposed so that light from the light source that has illuminated the object and is traveling from the object passes through the collection lens and travels along a collection path;
   (c) a beam splitter that is disposed in the collection path so that light from the light source that is scattered from the object is directed along a different path, while light that is emitted by the object continues through the beam splitter along the collection path;
   (d) a spectral dispersing element disposed beyond the beam splitter in the collection path, said spectral dispersing element spectrally dispersing the light emitted by the object, producing spectrally dispersed light;

(e) an imaging lens disposed to receive the spectrally dispersed light, producing an image thereof;

(f) a cylindrical lens disposed to receive the light scattered from the object, said cylindrical lens having a central axis around which the cylindrical lens is curved, said central axis being generally orthogonal to a direction of the relative movement between the object and the imaging system, so that the cylindrical lens produces a scattered pattern image of the object along a direction that is substantially parallel to said central axis of the cylindrical lens; and (g) at least one time delay integration (TDI) detector disposed to receive the image produced by the imaging lens, producing an output signal that is indicative of at least one characteristic of the object, and to receive the scattered pattern image produced by the cylindrical lens, producing a different output signal that is indicative of at least one other characteristic of the object, said at least one TDI detector producing said output signals by integrating light from the object over time while the object is moving.

33. The imaging system of claim 32, wherein the object is entrained within a fluid stream that moves the object past the first and the second collection lens.

34. The imaging system of claim 32, wherein the object is carried on a support.

35. The imaging system of claim 32, further comprising at least one beam conditioning lens disposed so that the light scattered by the object passes therethrough before reaching the cylindrical lens, said at least one beam conditioning lens improving a quality of the scattered pattern image on said at least one TDI detector.

36. The imaging system of claim 32, wherein a portion of said at least one TDI detector receives the scattered pattern image, and a different portion of said at least one TDI detector receives the image produced by the imaging lens from the spectrally dispersed light.

37. The imaging system of claim 36, wherein said at least one TDI detector responds to said images of the object by producing signals that propagate through said at least one TDI detector.

38. The imaging system of claim 37, wherein propagation rates of the signals through said at least one TDI detector are synchronized with a motion of the scattered pattern image and of the image of the object on said at least one TDI detector, while the relative movement between the object and the imaging system occurs.

39. The imaging system of claim 37, wherein propagation rates of the signals through said at least one TDI detector are not synchronized with a motion of the scattered pattern image and of the image of the object on said at least one TDI detector produced from the spectrally dispersed light, while the relative movement between the object and the imaging system occurs.

40. The imaging system of claim 32, wherein said dispersion element comprises a diffraction grating.

41. The imaging system of claim 32, wherein the beam splitter comprises a dichroic element that reflects the light scattered by the object and transmits the light emitted by the object.

42. The imaging system of claim 32, wherein the imaging lens images the spectrally dispersed light on a first TDI detector, and the cylindrical lens images the scattered pattern image on a second TDI detector.

43. A method for determining one or more characteristics of a moving object from an image of the object in which at least one component of the object is detected, while there is relative movement between the object and the imaging system, comprising the steps of:

(a) focusing light from the object along a collection path that is in a different direction than the relative movement between the object and the imaging system. said light traveling along the collection path being substantially collimated;

(b) dispersing the light that is traveling along the collection path, producing dispersed light;

(c) focusing the dispersed light to produce an image, said image clearly separately distinguishing components included in the object;

(d) providing a time delay integration (TDI) detector disposed to receive the image; and (e) analyzing an output signal from the TDI detector to determine at least one characteristic of the object.

44. The method of claim 43, wherein the step of dispersing the light comprises the step of spectrally dispersing the light.

45. The method of claim 43, wherein the image of the object produced by the step of focusing moves across the TDI detector, while the relative movement between the object and the imaging system occurs.

46. The method of claim 43, wherein the light from the object comprises an unstimulated emission from the object.

47. The method of claim 43, further comprising the steps of:

(a) providing a light source; and (b) illuminating the object with incident light from the light source while the object is moving.

48. The method of claim 47, wherein the object scatters the incident light, said light that is scattered from the object at least in part passing through the collection lens.

49. The method of claim 47, wherein the incident light illuminating the object stimulates the object to em it the light from the object that is focussed along the collection path.

50. The method claim 47, wherein the incident light is at least partially absorbed by the object, so that the light that is foussed along the collection path does not include light absorbed by the object.

51. The method of claim 47, wherein the light focussed along the collection path is the incident light produced by the light source that has been reflected from the object .

52. The method of claim 47, where in the light source comprises at least one of:

(a ) a coherent light source;

(b) a non-coherent light source;

(c) a pulsed light source; and (d) a continuous light source.

53. The method of claim 43, further comprising the step of entraining the object within a fluid stream that moves the object.

54. The method of claim 43, further comprising the step of carrying the object on a substrate during the step of focusing the light from the object along the collection path.

55. The method of claim 43, wherein the TDI detector responds to the imag(e of the object by producing a signal that propagates through the TDI detector.

56. The method of claim 55, further comprising the step of synchronizing a motion of the image of the object on the TDI detector with a propagation rate of the signal through the TDI detector, while the image of the object moves over the TDI detector.

57. The met hod of claim 43, further comprising the step of preventing extraneous light from reaching the TDI detector by transmitting substantially only the light from the object along the collection path.

58. A method for determining one or more characteristics of an object from a moving scattered pattern image of the object, comprising the steps of:
   (a) providing and positioning a light source to produce light that is incident on the object;
   (b) focusing light from the light source that is scattered from the object, along a collection path;
   (c) providing a cylindrical lens disposed in the collection path;
   (d) producing a scattered pattern image of the object with the cylindrical lens;
   (e) providing a time delay integration (TDI) detector disposed to receive the scattered pattern image produced by the cylindrical lens; and
   (f) analyzing an output signal from the TDI detector that has been produced by integrating light from at least a portion of the object over time, as the scattered pattern image of the object moves over the TDI detector.

59. The method of claim 58, wherein the TDI detector includes a plurality of light sensitive regions arranged in an array of rows and columns, further comprising the step of distributing said scattered pattern image along either a row or a column of the array.

60. The method of claim 58, further comprising the steps of:
   (a) illuminating a plurality of objects with the light emitted by the light source;
   (b) forming a plurality of separate scattered pattern images on the TDI detector; and
   (c) analyzing signals produced by the TDI detector in response to the separate scattered pattern images of the plurality of objects, each signal indicating at least one characteristic of a different one of the plurality of objects.

61. The method of claim 58, further comprising the step of entraining the object within a fluid stream that moves the object.

62. The method of claim 58, further comprising the step of synchronizing a motion of the scattered pattern image of the object on the TDI detector with a propagation rate of a signal through the TDI detector as the scattered pattern image of the object moves over the TDI detector.

63. The method of claim 58, further comprising the step of carrying the object on a support during the step of illuminating the object with light.

64. The method of claim 58, wherein the light source comprises at least one of:
   (a) a coherent light source;
   (b) a non-coherent light source;
   (c) a pulsed light source; and
   (d) a continuous light source.

65. The method of claim 58, further comprising the step of distributing the scattered pattern image over the TDI detector along a line aligned with a central axis of the cylindrical lens.

66. A method for determining characteristics of an object from images of the object, wherein components of the object are detected in the images while the images of the object move, comprising the steps of:
   (a) focusing light from the object along a first collection path in which the light is substantially collimated, and along a second collection path in which the light is substantially collimated, said second collection path being in a different direction than the first collection path;
   (c) producing first dispersed light from the light traveling along the first collection path;
   (d) producing an image from the first dispersed light;
   (e) providing a first time delay integration (TDI) detector disposed to receive the image;
   (f) analyzing a first output signal from the first TDI detector produced in response to the image of the first dispersed light by integrating the first dispersed light from at least a portion of the object over time while the image of the object is moving over the first TDI detector;
   (g) producing second dispersed light from the light traveling along the second collection path;
   (h) producing an image from said second dispersed light said image clearly separately distinguishing components included in the object;
   (i) providing a second TDI detector disposed to receive the image produced from the second dispersed light; and
   (j) analyzing a second output signal from the second TDI detector that was produced in response to the image of the second dispersed light by integrating the second dispersed light from at least a portion of the object over time while the image of the object is moving over the second TDI detector, said steps of analyzing the first and second output signals determining at least one characteristic of the object.

67. The method of claim 66, wherein the light emitted from the object is stimulated by light from a light source that is incident on the object.

68. The method of claim 66, further comprising the step of entraining the object within a fluid stream that moves the object.

69. The method of claim 66, further comprising the step of carrying the object on a support.

70. A method for determining characteristics of an object from images of the object, while the images of the object are moving, comprising the steps of:
   (a) providing a light source that emits light incident on the object;
   (b) focusing light from the object along a collection path;
   (c) splitting light scattered from the object apart from light that is emitted by the object and directing the light scattered from the object along a different path than the collection path;
   (d) spectrally dispersing the light emitted by the object to produce spectrally dispersed light;
   (e) producing an image of the spectrally dispersed light;
   (f) providing a cylindrical lens disposed to receive the light scattered from the object;
   (g) using the cylindrical lens to produce a scattered pattern image of the object;
   (h) providing a time delay integration (TDI) detector disposed to receive the image produced from the spectrally dispersed light, and to receive the scattered pattern image produced by the cylindrical lens;
   (i) analyzing output signals from the TDI detector to determine at least one characteristic of the moving object for each image by integrating light from the object over time while the images of the object move over the TDI detector.

71. The method of claim 70, further comprising the step of entraining the object within a fluid stream.

72. The method of claim 70, further comprising the step of carrying the object on a support.

73. The method of claim 70, wherein a portion of the TDI detector receives the scattered pattern image, and a different portion of the TDI detector receives the image produced from the spectrally dispersed light.

74. The method of claim 70, wherein the TDI detector responds to said images of the object by producing signals that propagate through the TDI detector.

75. The method of claim 70, further comprising the step of synchronizing a motion of the scattered pattern image and of the image of the object on the TDI detector produced by imaging the spectrally dispersed light with propagation rates of the signals through the TDI detector, as the images of the object move over the TDI detector.

76. The method of claim 70, wherein the step of splitting comprises the step of using a dichroic element to reflect the light scattered by the object and to transmit the light emitted by the object.

* * * * *

UNITED STATES PATENT AND TRADEMARK OFFICE
CERTIFICATE OF CORRECTION

PATENT NO. : 6,249,341 B1
DATED : June 19, 2001
INVENTOR(S) : Basiji et al.

It is certified that error appears in the above-identified patent and that said Letters Patent is hereby corrected as shown below:

Column 6,
Line 32, after "FIGURE 6" insert -- is --

Column 8,
Line 12, "arc" should read -- are --
Line 17, "arc" should read -- are --

Column 11,
Line 26, "spectrallydecomposed" should read -- spectrally-decomposed --

Column 16,
Line 63, "arc" should read -- are --

Column 17,
Line 1, "spots216" should read -- spots 216 --

Column 22, claim 49,
Line 36, "em it" should read -- emit --

Column 22, claim 51,
Line 44, "object ." should read -- object. --

Column 22, claim 52,
Line 45, "where in" should read -- wherein --

Column 22, claim 55,
Line 59, "imag(e" should read -- image --

UNITED STATES PATENT AND TRADEMARK OFFICE
CERTIFICATE OF CORRECTION

PATENT NO. : 6,249,341 B1
DATED : June 19, 2001
INVENTOR(S) : Basiji et al.

It is certified that error appears in the above-identified patent and that said Letters Patent is hereby corrected as shown below:

<u>Column 22, claim 57,</u>
Line 66, "met hod" should read -- method --

Signed and Sealed this

Sixteenth Day of April, 2002

Attest:

JAMES E. ROGAN
*Attesting Officer*       *Director of the United States Patent and Trademark Office*